(12) United States Patent
Herzog et al.

(10) Patent No.: US 7,772,579 B2
(45) Date of Patent: Aug. 10, 2010

(54) METHOD AND APPARATUS FOR SIMULTANEOUSLY MEASURING A THREE DIMENSIONAL POSITION OF A PARTICLE IN A FLOW

(75) Inventors: William D. Herzog, Groton, MA (US); Antonio Sanchez-Rubio, Lexington, MA (US); Gregory G. Cappiello, Windham, NH (US); Ronald H. Hoffeld, Cambridge, MA (US); Shane M. Tysk, Arlington, MA (US); Vincenzo Daneu, Woburn, MA (US); Thomas H. Jeys, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 87 days.

(21) Appl. No.: 11/804,589

(22) Filed: May 18, 2007

(65) Prior Publication Data

US 2008/0068605 A1 Mar. 20, 2008

Related U.S. Application Data

(60) Provisional application No. 60/802,087, filed on May 18, 2006, provisional application No. 60/927,832, filed on May 4, 2007.

(51) Int. Cl.
*G01N 15/06* (2006.01)
*G01N 21/49* (2006.01)
*G01N 21/85* (2006.01)

(52) U.S. Cl. ............... 250/574; 250/222.2; 250/559.29; 73/170.17; 73/170.21; 73/861.06; 356/28

(58) Field of Classification Search .................. 250/574, 250/222.2, 559.29; 73/170.17, 170.21, 861.06; 356/28

See application file for complete search history.

(56) References Cited

U.S. PATENT DOCUMENTS 4,643,566 A 2/1987 Ohe et al.

(Continued)

FOREIGN PATENT DOCUMENTS

DE 39 31 119 C1 4/1991

(Continued)

OTHER PUBLICATIONS

R. M. Huffaker, "Laser Doppler detection systems for gas velocity measurement," Appl. Opt. vol. 9, No. 1, 1026-1039 (Jan. 1970).

(Continued)

*Primary Examiner*—Seung C Sohn
(74) *Attorney, Agent, or Firm*—Hamilton, Brook, Smith & Reynolds, P.C.

(57) ABSTRACT

Particle detection systems without knowledge of a location and velocity of a particle passing through a volume of space, are less efficient than if knowledge of the particle location is known. An embodiment of a particle position detection system capable of determining an exact location of a particle in a fluid stream is discussed. The detection system may employ a patterned illuminating beam, such that once a particle passes through the various portions of the patterned illuminating beam, a light scattering is produced. The light scattering defines a temporal profile that contains measurement information indicative of an exact particle location. However, knowledge of the exact particle location has several advantages. These advantages include correction of systematic particle measurement errors due to variability of the particle position within the sample volume, targeting of particles based on position, capture of particles based on position, reduced system energy consumption and reduced system complexity.

30 Claims, 19 Drawing Sheets

U.S. PATENT DOCUMENTS

| | | | |
|---|---|---|---|
| 5,282,151 | A | 1/1994 | Knollenberg |
| 5,793,478 | A | 8/1998 | Rader et al. |
| 5,883,707 | A | 3/1999 | Arndt et al. |
| 5,920,388 | A | 7/1999 | Sandberg et al. |
| 6,867,410 | B2 * | 3/2005 | Sasaki et al. ............... 250/574 |
| 7,471,393 | B2 | 12/2008 | Trainer |
| 2001/0040214 | A1 | 11/2001 | Friedman et al. |
| 2002/0122167 | A1 | 9/2002 | Riley et al. |
| 2006/0066837 | A1 | 3/2006 | Ortyn et al. |
| 2006/0204071 | A1 | 9/2006 | Ortyn et al. |

FOREIGN PATENT DOCUMENTS

| | | |
|---|---|---|
| DE | 198 34 583 C1 | 12/1999 |
| DE | 199 26 494 A1 | 12/2000 |
| DE | 199 54 702 A1 | 5/2001 |
| EP | 0 467 127 A2 | 1/1992 |
| JP | 61-29737 | 2/1986 |
| WO | WO 98/41876 | 9/1998 |
| WO | WO 01/79861 A1 | 10/2001 |
| WO | WO 2005/090945 A1 | 9/2005 |
| WO | WO 02/088673 A2 | 11/2008 |

OTHER PUBLICATIONS

D.T. Suess and K. A. Prather, "Mass spectrometry of aerolsols", Chem. Rev. 99, 3007-3035 (1999).

Y.L. Pan, S. Holler, R. K. Chang, S. C. Hill, R. G. Pinnick, S. Niles, and J. R. Bottiger, "Single-shot fluorescence spectra of individual micrometer-sized bioaerosols illuminated by a 351- or a 266-nm ultraviolet laser," Opt. Lett. vol. 24, No. 1, pp. 116-118 (Jan. 1999).

K. Davitt, Y.-K. Song, W. Patterson, III, A. Nurmikko, M. Gherasimova, J. Han, Y.-L. Pan, and R. Chang, "290 and 340 nm UV LED arrays for fluorescence detection from single airborne particles," Opt. Express vol. 13, No. 23, pp. 9548-9555 (Nov. 2005).

D. R. Burnham and D. McGloin, "Holographic optical trapping of aerosol droplets," Opt. Express vol. 14, No. 9, pp. 4175-4181 (2006).

K. G. Barlett and C. Y. She, "Single-particle correlated time-of-flight velocimeter for remote wind-speed measurement," Opt. Lett. vol. 1, No. 5, pp. 175-177 (Nov. 1977).

William D. Herzog, Shane M. Tysk, David W. Tardiff, Gregory G. Cappiello, Jasaon M. Jong, Thomas H. Jeys, Ronald H. Hoffeld, Antionio Sanchez and Vincenzo Daneu, "Measurement of aerosol-particle trajectories using a structured laser beam," Appl. Opt. vol. 46, No. 16, pp. 3150-3155 (Jun. 2007).

International Search Report for PCT/US2007/012034 dated Jul. 2, 2008.

International Search Report from PCT/US2008/001793 mailed Nov. 21, 2008.

International Search Report and Written Opinion from PCT/US2007/012034, mailed Feb. 7, 2008.

International Search Report and Written Opinion from PCT/US2007/012017, mailed May 7, 2008.

International Search Report and Written Opinion from PCT/US2008/001793, mailed Nov. 21, 2008.

Office Action from U.S. Appl. No. 11/804,593, mailed on Dec. 10, 2009.

* cited by examiner

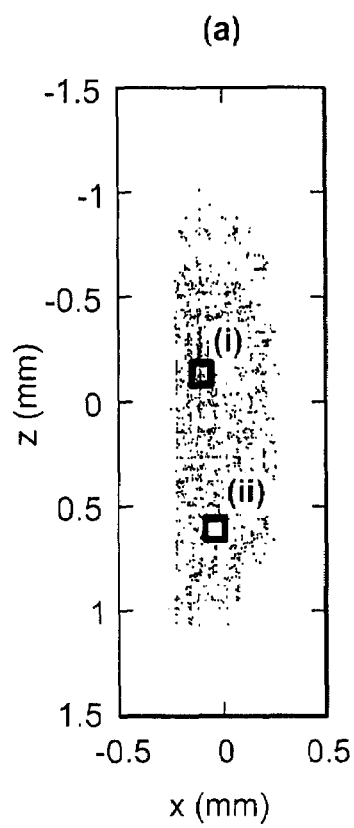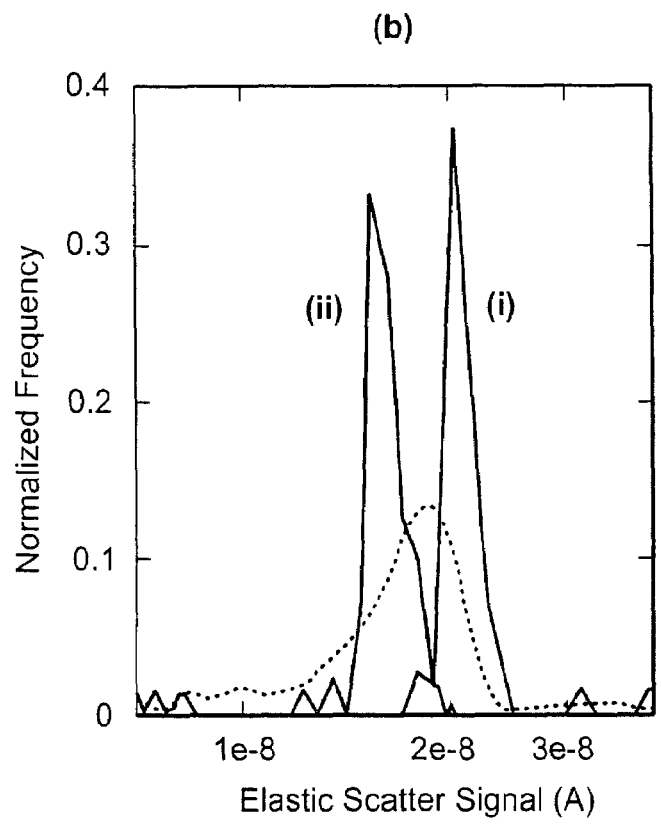
FIG. 8A
FIG. 8B

METHOD AND APPARATUS FOR SIMULTANEOUSLY MEASURING A THREE DIMENSIONAL POSITION OF A PARTICLE IN A FLOW

RELATED APPLICATION

This application claims the benefit of U.S. Provisional Application No. 60/802,087, filed on May 18, 2006, and claims the benefit of U.S. Provisional Application No. 60/927,832 filed on May 4, 2007, entitled "Measurement of Aerosol-Particle Trajectories Using a Structured Laser Beam." The entire teachings of the above applications are incorporated herein by reference.

GOVERNMENT SUPPORT

The invention was supported, in whole or in part, by a grant FA8721-05-C-0002 from the U.S. Department of the Army. The Government has certain rights in the invention.

BACKGROUND OF THE INVENTION

The ability to detect and classify small particles in a fluid stream has been of great use in many fields. For example, the detection of harmful particles or biological agent particles in air (outdoors or inside a building) or in water (a city water supply) may require monitoring the air or water for such particles.

SUMMARY OF THE INVENTION

Aerosol and hydrosol particle detection systems typically do not determine the exact location of an individual particle as it passes through the detection system sample volume. However, knowledge of the exact particle location has several advantages. These advantages include correction of systematic particle measurement errors due to variability of the particle position within the sample volume, targeting of particles based on position, capture of particles based on position, reduced system energy consumption and reduced system complexity.

Real-time measurement of the properties of aerosol particles is important for applications such as flow visualization, detection of biological warfare agents, characterization of atmospheric pollutants, and clean-room monitoring. Laser Doppler Velocimetry (LDV) systems have been successfully utilized for decades to characterize gas-flow dynamics of the atmosphere and systems such as wind tunnels and jet flows. As a final example of a need for particle cuing and localization, given the minuscule interaction volumes of optical tweezers, a knowledge of the particle trajectory may be critical to efficiently populate trapping volumes.

Useful to the design of many aerosol instruments is the localization of the aerosol particles within a well-defined measurement, or interaction, volume where reproducible and accurate measurements can be made. For example, time-of-flight laser velocimetry is a common localization technique that has long been used to cue aerosol mass spectrometers to the presence of a particle in the interaction region.

In the case of single-particle aerosol optical spectroscopy, use of crossed laser beams to define the sample volume is useful to the measurement of fluorescence spectra of single aerosol particles with useful signal-to-noise ratio. As a part of more recent efforts to develop compact single-particle aerosol fluorescence sensors, multiple LEDs are cured and synchronously activated to illuminate the aerosol particle along its trajectory through the instrument.

An apparatus and method for simultaneously providing particle velocity and position measurements in three dimensions is disclosed. The apparatus and method may involve projecting a spatial pattern of light, using a Structured Laser Beam (SLB), into the path of an aerosol stream. As a particle traverses the SLB it may elastically scatter light onto a photo-detector, which, in turn, provides data to a processor, or any other similar device, to record the scattered light as a time-dependent waveform.

The SLB may be designed such that all possible particle trajectories result in a unique temporal waveform. The waveform may then be decoded to determine the particle position and velocity. The particle detection apparatus, and corresponding method of operation, has the benefits of very rapidly providing high-fidelity trajectory information using only a single laser source and a single photo-detector.

The apparatus for determining a position of a particle in a flow may include a light source to generate an illuminating beam to travel in a first dimension, and to produce an illumination pattern in first, second, and third dimensions. The light source may be a coherent light source or an incoherent light source. The apparatus may also include a detector to detect a temporal profile of scattered light produced by the particle in the flow, traveling in the flow in the third dimension, passing through the illumination pattern. The apparatus also includes a position determining unit to determine, from the temporal profile, a position of the particle in at least two dimensions in a simultaneous manner.

The apparatus may further include a masking element that may be configured to produce the illumination pattern once the masking element is illuminated by the light source. The masking element may be a mask or a diffractive optic. The masking element may be further configured to define the illumination pattern with a pattern of varying intensity or other any other property of light that may be useful in forming an illumination pattern, for example, polarization.

The masking element may be used to form a first portion of the illumination pattern at a first angle relative to an axis of propagation of the illuminating beam, and at a second angle relative to an axis along the second dimension. The masking element may be used to form a second portion of the illumination pattern at a third angle relative to the axis of propagation of the illuminating pattern, and at a fourth angle relative to the axis along the second dimension.

The masking element may be further configured to form a third and fourth portion of the illumination beam, the third and fourth portion at a fifth and sixth angle, respectively, relative to an axis of propagation of the illuminating beam, and at a seventh and eight angle, respectively, relative to an axis along the second dimension.

A velocity of the particle may be determined as a function of a geometrical relationship of at least two portions of a plurality of portions of the illumination pattern, and a measurement of effects imparted in the temporal profile, caused by the particle's passing through the at least two portions of the plurality of portions of the illumination pattern and a geometrical relationship of the plurality of portions of the illumination pattern.

A time dependent position of the particle in the third dimension may also be determined. The time dependent position may be based on a measurement of effects imparted in the temporal profile, caused by the particle's passing through the plurality of portions of the illumination pattern and a geometrical relationship of the plurality of portions of the illumination pattern.

The position of the particle in the second dimension may also be determined. The position of the particle in the second dimension may be based on a measurement of effects imparted in the temporal profile, caused by the particle's passing through the plurality of portions of the illumination pattern and a geometrical relationship of the plurality of portions of the illumination pattern.

The position of the particle in the first dimension may be determined. The position of the particle in the first dimension may be based on a measurement of effects imparted in the temporal profile, caused by comparison of the timing signals the particle's passing through the plurality of portions of the illumination pattern and a geometrical relationship of the plurality of portions of the illumination pattern.

The temporal profile may be a first temporal profile, wherein the masking element further includes a first portion employed in generating a first illumination pattern to obtain the first temporal profile and at least one other portion employed in generating a second illumination pattern to obtain at least one second temporal profile to be detected at a later time.

The apparatus may also include a velocity determining unit that may be configured to determine a time rate of change in the at least two dimensions and characterize a velocity of the particle in the at least two dimensions. The position determining unit may be further configured to refine a previously determined position of the particle in the at least two dimensions, from the first temporal profile, with the at least one other temporal profile, detected at a later time.

The processing unit may also be configured to simultaneously determine a position of the particle in the first dimension, second dimension, a time dependent position in the third dimension, and a particle velocity. The velocity determining unit may be configured to determine a rate of change of the position of the particle in the first and second dimensions, and the time dependent position in the third dimension, and determine an updated particle velocity in the first and second dimensions. The position determining unit may be configured to refine a previously determined position of the particle in the first and second dimensions, and the time dependent position in the third dimension, with the at least one other temporal profile detected at a later time.

An acceleration determining unit may be configured to determine a particle acceleration in the third dimension. The position, velocity, and/or acceleration determining units may further be configured to determine a motion of the particle with the inclusion of changes in particle motion due to external forces exerted on the particle. The position, velocity, and/or acceleration determining units may be further configured to detect the presence of a biologic or chemical agent. The position, velocity, and/or acceleration determining units may also be configured to determine a plurality of calibration factors for the normalization of subsequent measurements.

The apparatus may further include an optical element, coupled to the masking element and configured to project a first portion of the illuminating beam at a first angle relative to an axis of propagation of the illuminating beam. The optical element may be further configured to project a second portion of the illuminating beam at a second angle relative to the axis of propagation of the illuminating beam.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 8A and 8B are graphical examples of measured data obtained using the measurement system of FIG. 6;

DETAILED DESCRIPTION OF THE INVENTION

A description of example embodiments of the invention follows.

Figure 1:
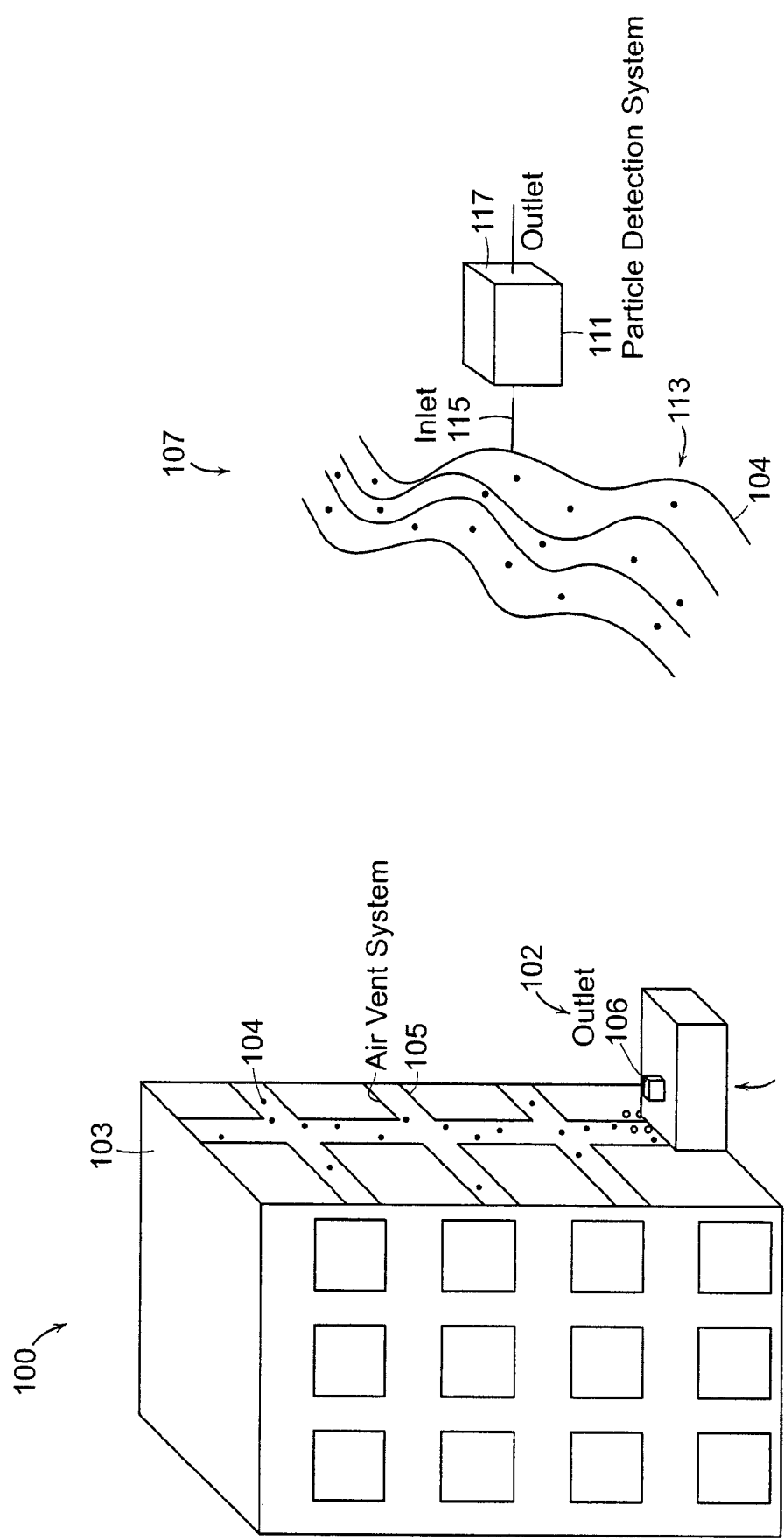
FIGS. 1A and 1B are diagrams with examples of particle detection systems.

FIG. 1A provides an example 100 of a particle detection system 101. The particle detection system 101 may be situated to detect particles 104 in an airvent system 105 of a building 103. The particle detection system 101 includes an inlet (not shown) in which an airflow enters the particle detection system 101. An outlet 106 of the particle detection system 101 may be used as a pathway to shunt the airflow if particles 102 detected are deemed unsafe for breathing. Otherwise, the airflow can continue into the airvent system 105.

As another example, a liquid stream may also need to be evaluated. For instance, a water reservoir may need to be continuously monitored to ensure harmful particles are not introduced into a water supply.

FIG. 1B provides an example 107 of a particle detection system 111 detecting particles 113 in a liquid stream 109. The particle detection system 111 may include an inlet 115 used to supply a sample of the liquid flow 109 to the particle detection system 111. Once the liquid flow 109 has been checked for a presence of foreign particles, an outlet 117 may be used to remove the sample from the particle detection system 111.

Figure 2:
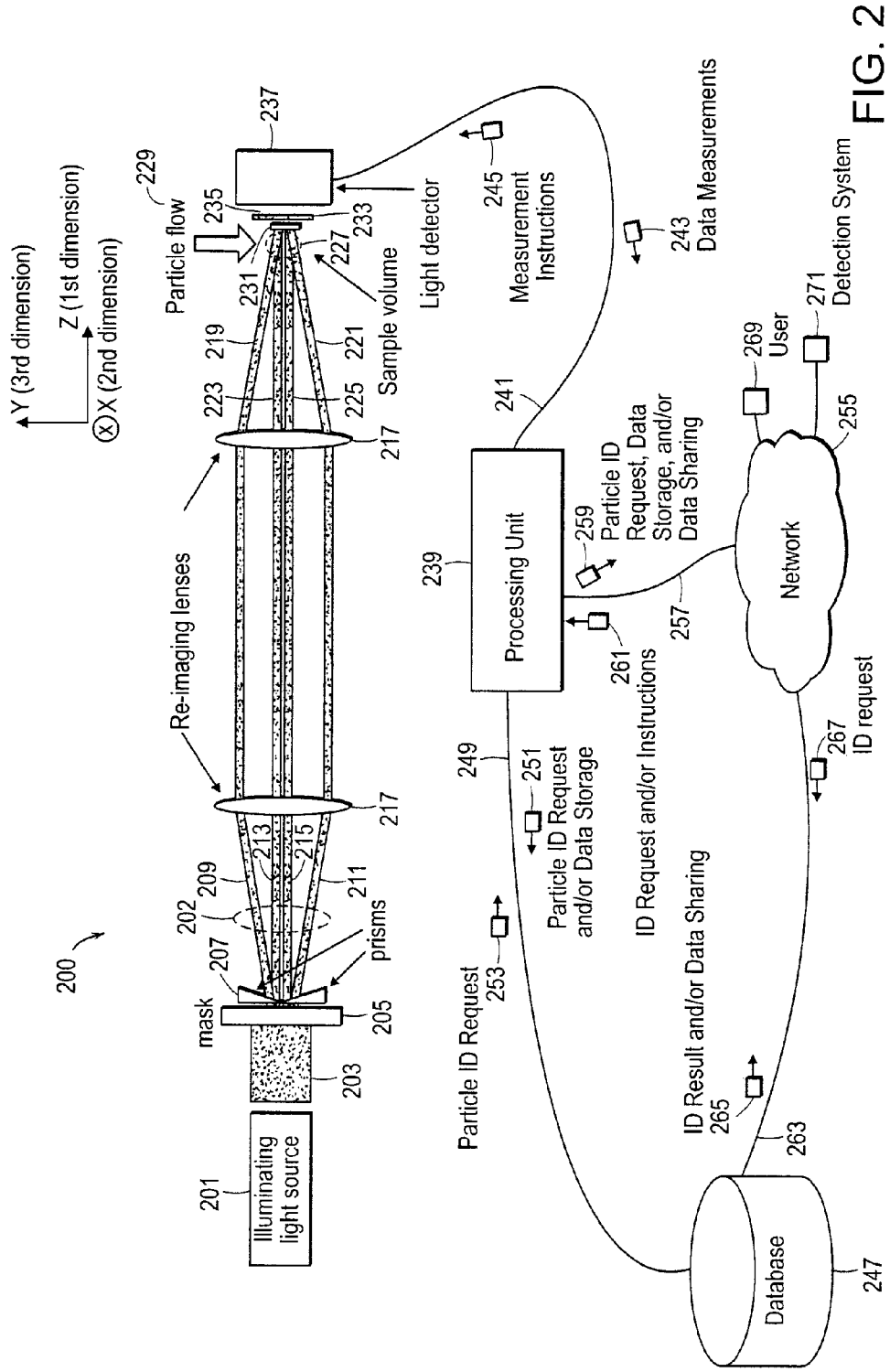
FIG. 2 is a schematic diagram of an overview of a structured laser beam detection system for determining a three dimensional position and velocity of a particle, according to an embodiment of the present invention.
Figure 3:
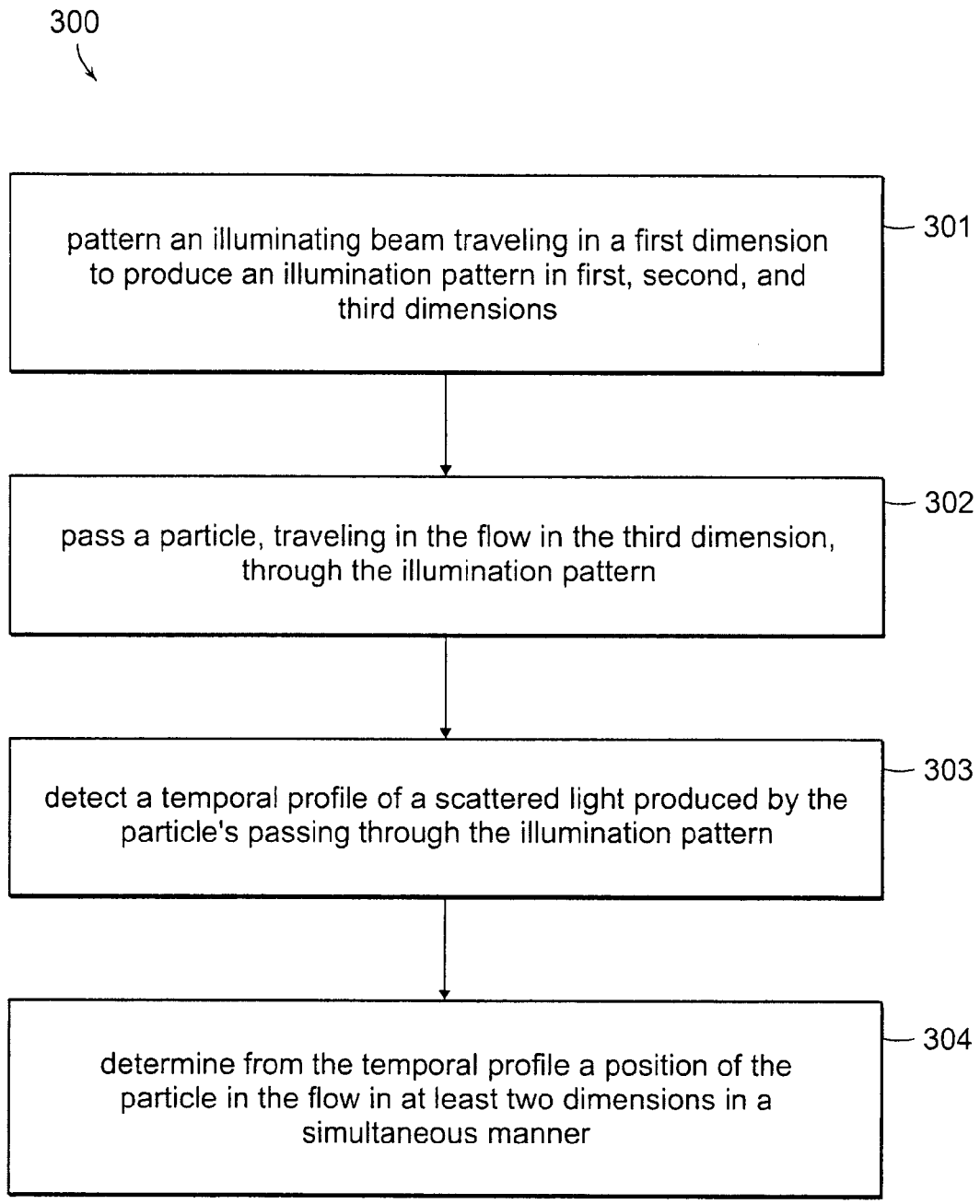
FIG. 3 is a flow diagram of an overview of operative steps of the detection system of FIG. 2.

FIG. 2 is a schematic diagram illustrating an example of a particle detection system 200 according to an embodiment of the present invention. FIG. 3 shows a flow diagram 300 of an overview of operations that may be taken by the detection system 200. Referring to FIG. 2 with references to FIG. 3, the particle detection system 200 may include a light source 201 configured to emit a propagating beam 203, also referred to herein as an "illuminating light beam," traveling in the z direction, or a first dimension. A masking element 205 may be coupled to the light source 201 to produce a structured laser beam (SLB) comprising a light beam pattern 202 also referred to herein as an "illuminating pattern," in z, x, and y dimensions, or first, second, and third directions, respectively (FIG. 3, 301).

The masking element 205 may be configured to define multiple portions 209, 211, 213, and 215 of the structured laser beam 202. An optical expanding element 207 (i.e., a prism) may be placed in proximity to the mask 205 and may be used to project at least one portion of the multiple laser beam sections at an angle As an example, the structured laser beam 202 may comprise a first and second portion 209 and 211, respectively, being configured at an angle with respect to the axis of propagation. A third and fourth portion 213 and 215, respectively, may be configured to propagate along the axis of propagation, in a parallel configuration, and may be rotated about the axis of propagation (i.e., the third and fourth portions, 213 and 215, may comprise an inclined configuration in the x axis or second dimension).

Re-imaging optics 217 in addition with a spatial filter, or mask, may be used to eliminate undesirable fringing and diffraction, thus providing a clean and near Gaussian distribution normal to the long axis of the propagating plane. As a result of the re-imaging optics 217, converging first and second portions 219 and 221, respectively, as well as converging third and fourth portions 223 and 225, respectively, may be focused onto a sample volume 227 comprising a flow of particles 229. As the particles pass through the structured beam (FIG. 3, 302), a light scattering 235 is produced. The particle light scattering 235 includes a temporal profile that may be used to obtain timing signals indicative of when the particle passed through the various portions of the illumination pattern. Using the timing signals and geometrical relationships of the SLB illumination pattern, the velocity and three dimensional position of the particle may be obtained.

A beam block 231 may be configured to block the structured beam, such that a light detector 237 does not receive light directly from the structured beam, therefore preventing saturation. A focusing element 233 may be used to focus the scattered light 235 onto the light detector 237 (FIG. 3, 303).

The light detector 237 may be coupled to a processing unit 239. The light detector 237 may be configured send data measurements 243 to the processing unit 239 in the form of an analog electrical signal. The processing unit 239 may include a position determining unit configured to determine the position of the particle in the first (z), second (x), and third (y) dimensions. The determined particle position may be based on the timing signals obtained from the temporal profile of the detected scattered light 235, as well as the geometrical properties of the illumination pattern (FIG. 3, step 304). The processing unit 239 may also include a velocity determining unit to determine the velocity of the particle, and an acceleration determining unit to determine the particle's acceleration in the sample volume.

The processing unit 239 may be configured to send measurement instructions 245 to the light detector 237 in the case that the light detector 237 includes an intelligent programmable configurable. The measurement instructions 245 may include, for example, on/off instructions. The light detector 237 and the processing unit 239 may be connected via a connection link 241. It should be appreciated that the connection link 241 may be a wired, optical, or wireless connection, or any other data transfer connection known in the art.

The processing unit 239 may also be connected to a database storage 247. The processing unit 239 may send the database storage 247 a particle identification request, and/or a data storage request 251. The data storage request 251 may include the data measurements 243, or representation thereof, provided by the light detector 237. The particle identification request may include a request to compare information stored in the database storage 247 with the obtained data measurements 243, optionally for the purpose of classifying and identifying the particles in the sample volume 227. The database storage 247 may send a particle identification result 253 to the processing unit 239. The particle identification result 253 may comprise a listing of possible particle matches with respect to the data measurements 243.

The processing unit 239 may also be coupled to a network 255. The processing unit 239 may send a particle identification request, a data storage request, and/or a data sharing request 259 to the network 255. The particle identification request and data sharing request 259 may be similar to the request 251 sent to the database storage 247. The data sharing request 259 may be a request to share data with a user 269 that may be connected to the network 255, or another detection system 271 that may be connected to the network 255. The network 255, or more specifically, a server or other network element (not shown) connected to the network 255, may also send a message 261 in the form of particle identification results, similar to the result 253 sent by the database storage 247, or instructions to the processing unit 239. The instructions 261 may comprise measurement instructions similar to the instructions 245 sent to the light detector 237.

The database storage 247 and the network 255 may also include a bidirectional data transfer connection 263. The database storage 247 may send identification results and/or a data sharing request 265 to the network 255. The network 255 may send an identification request 267 to the database storage 247. It should be appreciated that the data transfer connections 249, 257, and 263 between the processing unit and the data storage, the processing unit and the network, and the network and the data storage, respectively, may include or be supported by any data transmission link known in the art.

It should also be appreciated that the configuration shown in FIG. 2 of the particle detection system 200 is merely an example. Any other directional configuration may be employed, preferably with the first (z) (i.e., direction of beam propagation), second (x), and third (y) (i.e., direction of the flow of particles) dimensions orthogonal to one another. Furthermore, it should be appreciated that the analysis of particles in a air flow is used merely as an example. Particles in any type of fluid stream may be analyzed, for example air, liquid, vapor, or any other known forms of a fluid stream.

Figure 4A:
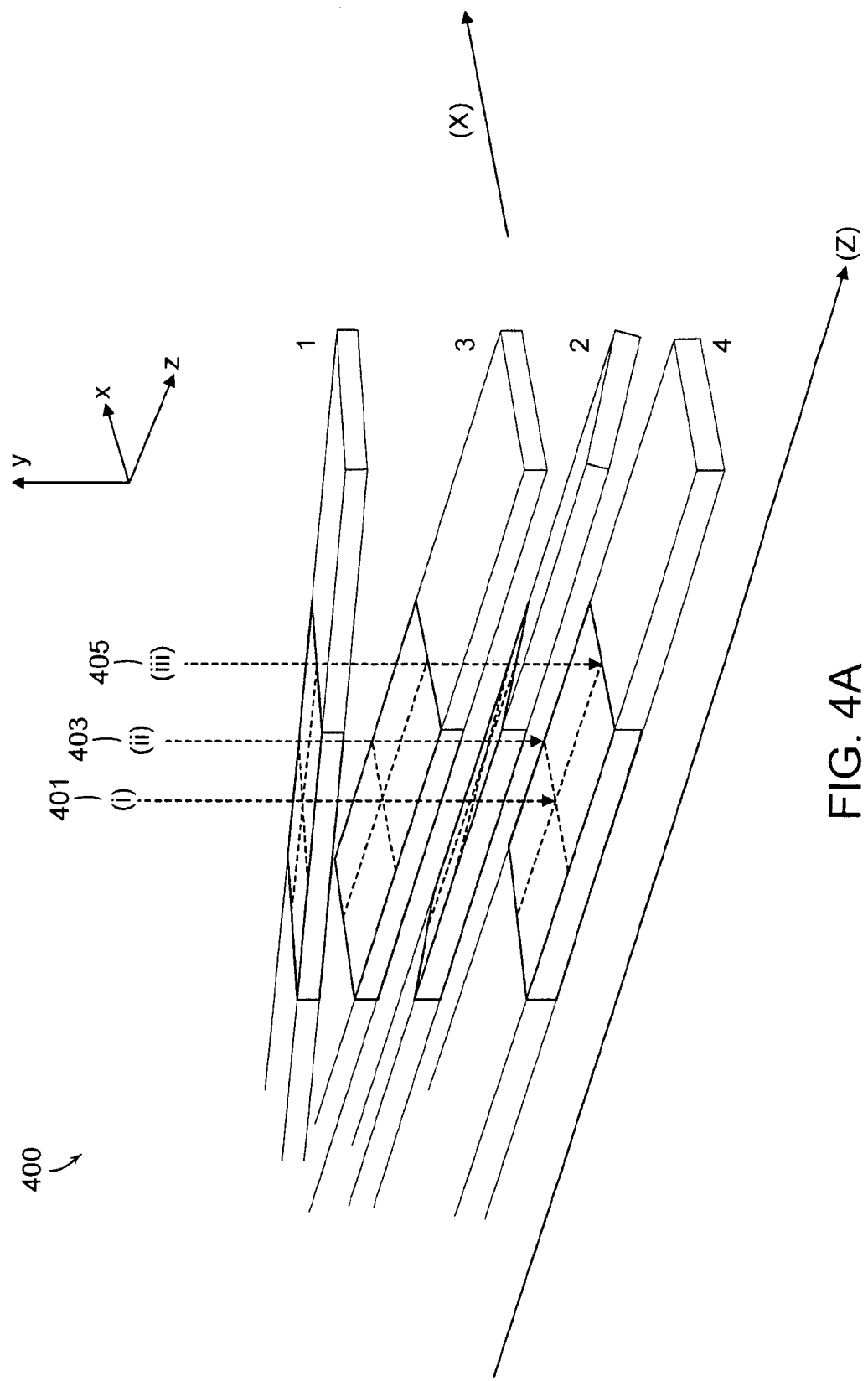
FIGS. 4A and 4B are diagrams of example geometrical configurations of the illumination pattern formed by the structured laser beam, according to an embodiment of the present invention.

FIG. 4A provides an example of the SLB 400. As was previously discussed in reference to FIG. 2, the SLB may comprise four portions. The first and second portions, labeled as (1) and (2) respectively, may be configured to propagate, in a diverging manner, along the z, or first, dimension at a respective angle. The first (1) and second (2) portions of the SLB may also comprise an angled incline in the x, or second, dimension.

The third (3) and fourth (4) portions may be configured to propagate, in a parallel orientation, along the z, or first, dimension at a substantially zero angle. The third (3) and fourth (4) portions may also comprise a substantially zero angle inclination with respect to the x, or second, dimension. It should be appreciated that the SLB configuration 400 is merely an example, the SLB may comprise any number of portions situated along any dimension and comprising a variety of angled inclinations. For example, the SLB may comprise any number of portions illuminated in a diverging manner.

Figure 4B:
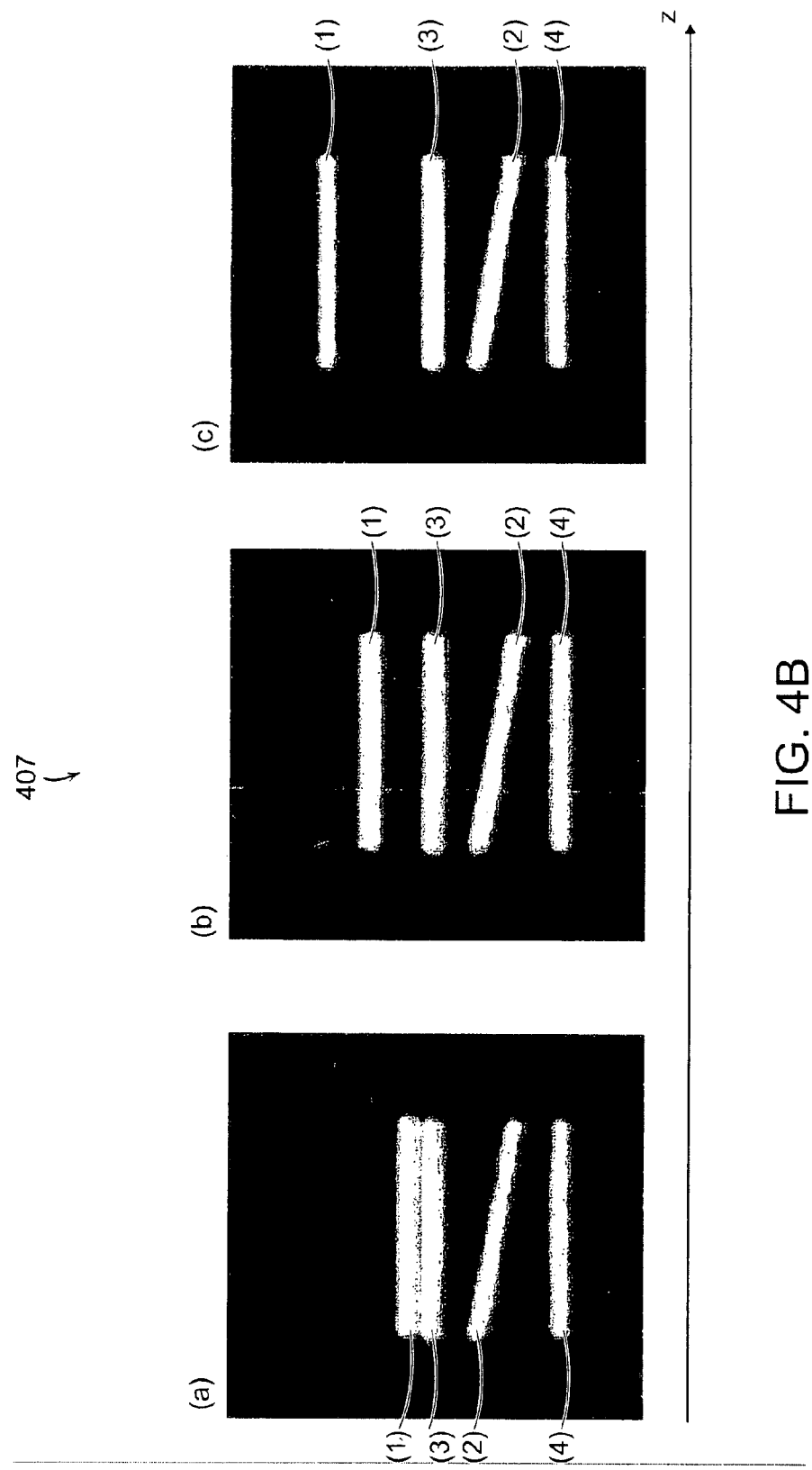

FIG. 4B depicts three cross-sectional views 407a-407c of the SLB, or illumination pattern, at different points along the z axis, or first dimension. The cross-sectional view 407a is closest to the light source, while the cross-sectional view 407c is farthest from the light source. Due to the fact the first (1) and the second (2) portions of the laser beam are angled along the first (z) dimension (or propagating in a diverging manner), as well as the second (x) dimension, at different places along the first (z) dimension, the distances between the first (1) and second (2) portion of the structured laser beam vary. For example, in a comparison of the cross-sectional views 407a and 407b, the first (1) and second (2) portions of the SLB have expanded, or diverged, as the SLB propagates along the positive first (z) dimension. The cross-sectional view 407c shows an even greater amount of divergence of the first (1) and second (2) portions of the SLB. The divergence of the first (1) and second (2) portions of the SLB may be caused by the optical expanding element, or the prism 207, shown in FIG. 2. Meanwhile, the third (3) and fourth (4) sections of the SLB may comprise a constant angle, with respect to the first (z) dimension, though out the SLB's propagation along the first (z) dimension. As the particle in the sample volume passes through the SLB, the particle will pass through all the portions of the illumination pattern. Therefore, timing signals indicative of when the particle passed through each portion of the illumination pattern may be obtained from the detected temporal profile.

Figure 4C:
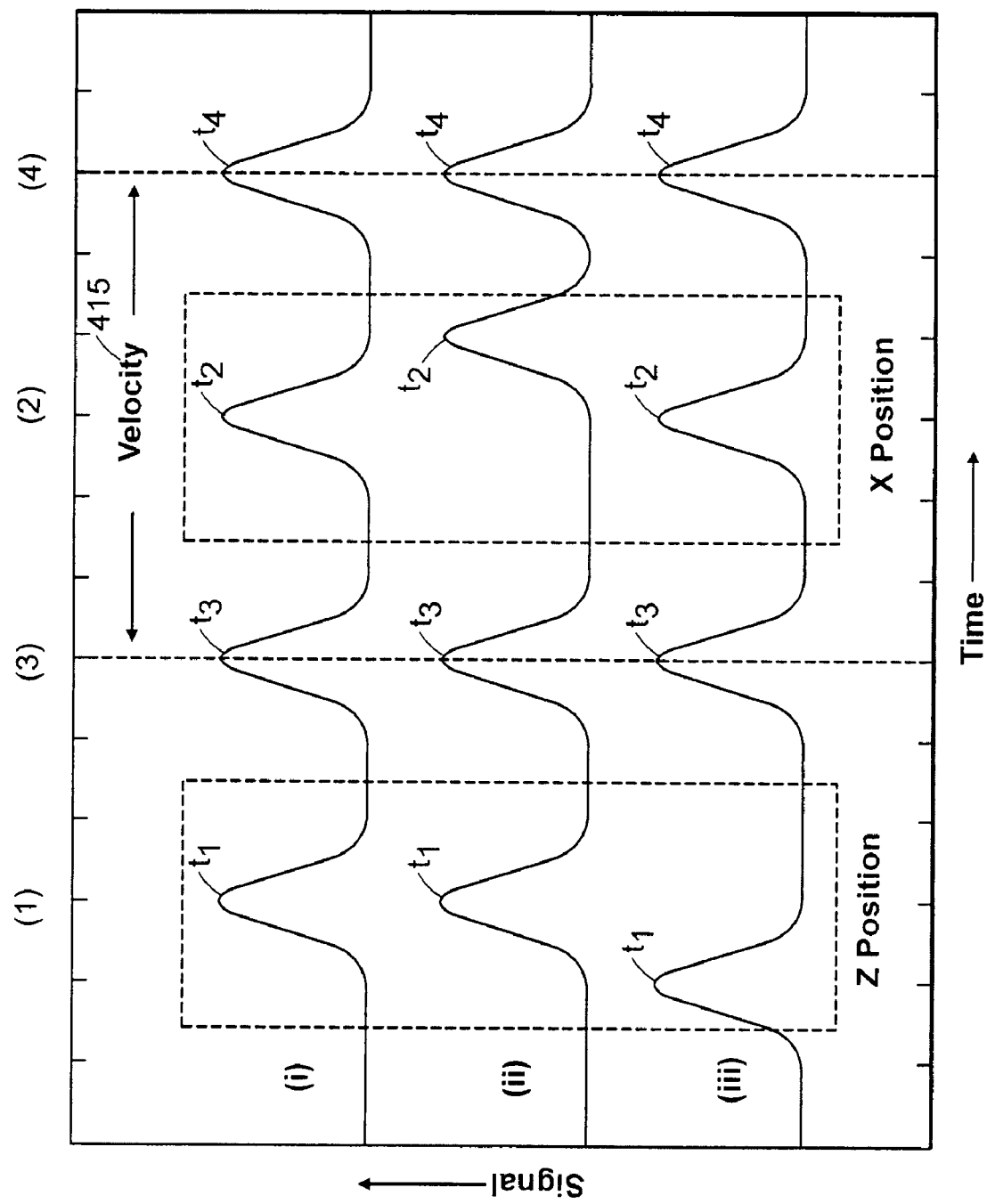
FIG. 4C is a schematic diagram of example measurement signals obtained using the structured laser beam of FIGS. 4A and 4B, according to an embodiment of the present invention.

FIG. 4C provides an illustrative example of timing measurements which may be obtained from the temporal profile included in the scattered light produced by the particle passing through the various portions of the SLB shown in FIG. 4A. The signal labeled (i) represents the particle 401 (FIG. 4A) passing through the portions (1)-(4) of the SLB. Each of the signals for the particles (i)-(iii) has four peaks $t_1$-$t_4$ representing the time the respective particle passed through the respective portion of the SLB. Note that the particle will pass through all the portions of the illumination pattern, therefore the timing signal will comprise as many peaks as there are portions.

The velocity 415 of the particle may be obtained by taking the difference between the time the particle passed through the third (3) portion of the SLB and the time the particle passed through the fourth (4) portion of the SLB (FIG. 4A). Since the third (3) and fourth (4) portion of the SLB comprise a constant, and substantially zero, angle with respect to the first (z) dimension through out the propagation of the SLB, the distance between the third (3) and fourth (4) portions of the SLB remain constant through out the first (z) dimension. Therefore, obtaining the velocity of the particle in the sample volume may be achieved without the knowledge of the particle position in the first (z), second (x), and third (y) dimensions. Thus, the equation for finding the particle velocity may be represented by the following:

$$v = t_3 - t_4 \qquad [1]$$

with $t_3$ and $t_4$ representing the time the particle passed through the third (3) and fourth (4) portions of the illumination pattern, respectively. It should be appreciated that the greater the of divergence or spacing between the various portions, the greater the velocity resolution will be. Similarly, the greater the slope of the diverging beam, the greater the spatial resolution will be. An increased spatial resolution may improve the efficiency of determining the particle position.

The position of the particle in the third (y) dimension is a time dependent position since the particle is traveling in the negative third (y) dimension. Therefore, the position of the particle in the third (y) dimension may be obtained with knowledge of the particle velocity. Once the particle has passed through either the first (1), second (2), third (3), or fourth (4) portion of the SLB, the time dependent position of the particle may be obtained since the particle velocity is known. Therefore, the motion of the particle moving in the negative third (y) dimension (FIG. 4A) may be predicted.

Figure 5A:
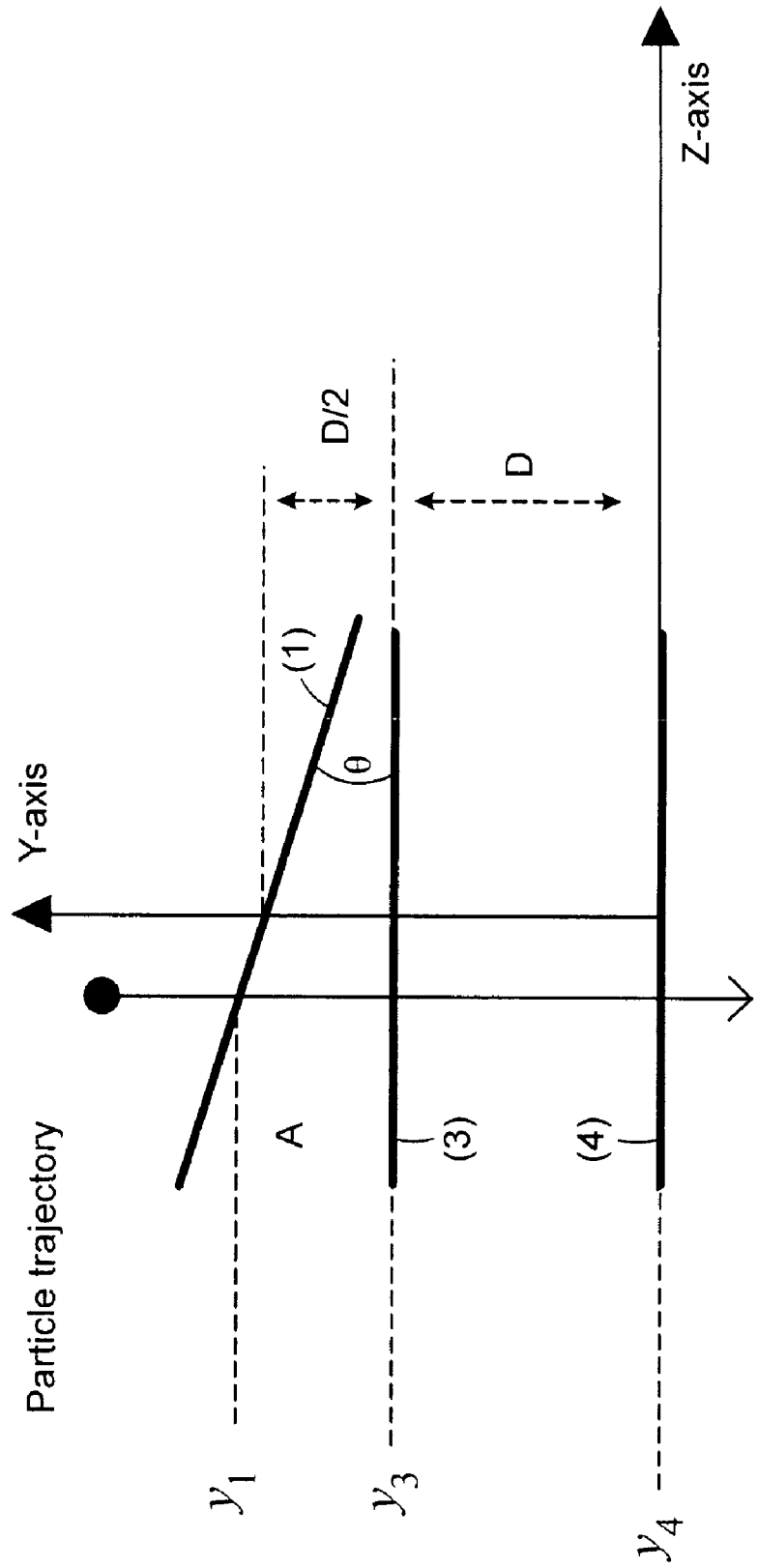
FIGS. 5A and 5B are illustrative examples of geometrical relationships of the illumination pattern employed in obtained a dimensional position of the particle, according to an embodiment of the present invention.

FIG. 5A illustrates the geometrical relationship of the SLB which may be employed in finding the position of the particle in the first (z) dimension. The position of the particle in the first (z) dimension may be obtained using the third (3), fourth (4), and either the first (1) or second (2) portions of the SLB. It should be appreciated that although FIG. 5A shows the third (3), fourth (4) and first (1) portions of the SLB being employed in finding the position of the particle in the first (z) dimension, the second (2) portion of the SLB may be employed instead of the first (1) portion.

The first (1) portion of the SLB comprises a sloped orientation in the first (z) dimension. The slope of the first (1) portion of the SLB in the first (z) dimension may be represented by:

$$y = mz + b \qquad [2]$$

where y represents the position of the particle in the third (y) dimension as the particle passes through the first (1) portion of the SLB, m represents the slope of the first (1) portion of the SLB in the third (y) dimension, z represents the position of the particle in the first (z) dimension as the particle passes through the first (1) portion of the SLB, and b represents the position where the first (1) portion of the SLB intercepts the axis in the third (y) dimension.

The slope of the first (1) portion of the SLB may be written in terms of θ and the value of the y axis intercept may be written in terms of D, the constant distance between the third (3) and the fourth (4) portions of the SLB (FIG. 5) yielding:

$$A = -\tan(\theta)z + \frac{D}{2} \qquad [3]$$

where A equals $y_2$-$y_3$, the difference in position of the particle intercepting the first (1) and third (3) portions of the SLB. Solving for z and substituting in D=2A and $$\frac{D}{2} = D - \frac{D}{2}$$

yields:

$$z = \frac{1}{\tan(\theta)}\left(A - \frac{D}{2}\right) \qquad [4]$$

Rearranging yields:

$$z = \frac{D}{\tan(\theta)} \left( \frac{A}{D} - \frac{1}{2} \right) \quad [5]$$

Substituting the values of D and A in terms of their y intercept values yields:

$$z = \frac{y_3 - y_4}{\tan(\theta)} \left( \frac{y_1 - y_3}{y_3 - y_4} - \frac{1}{2} \right) \quad [6]$$

Employing the relationship between distance, time and velocity:

$$d = vt \quad [7]$$

the following equation may be obtained:

$$y_i - y_j = v(t_i - t_j) \quad [8]$$

where the distance the particle traveled is represented by $y_i - y_j$ and the time taken for the particle to travel being represented by $t_i - t_j$. Employing the relationship of equation [8] into equation [6] yields:

$$z = \frac{v(t_3 - t_4)}{\tan(\theta)} \left( \frac{v}{v} \left( \frac{t_1 - t_3}{t_3 - t_4} \right) - \frac{1}{2} \right) \quad [9]$$

Simplifying equation [9] and substituting in for D ($D = y_3 - y_4$) yields:

$$z = \frac{D}{\tan(\theta)} \left( \left( \frac{t_1 - t_3}{t_3 - t_4} \right) - \frac{1}{2} \right) \quad [10]$$

Therefore, with knowledge of the constant distance D between the third (3) and fourth (4) portions of the SLB, the angle θ defined by the orientation of the first (1) portion of the SLB with respect to the first (z) dimension, the timing values (FIG. 4D) of the particle passing through the first (1), third (3), and fourth (4) portions of the SLB, and the particle velocity, the position of the particle in the first (z) dimension may be obtained in real time.

Figure 5B:
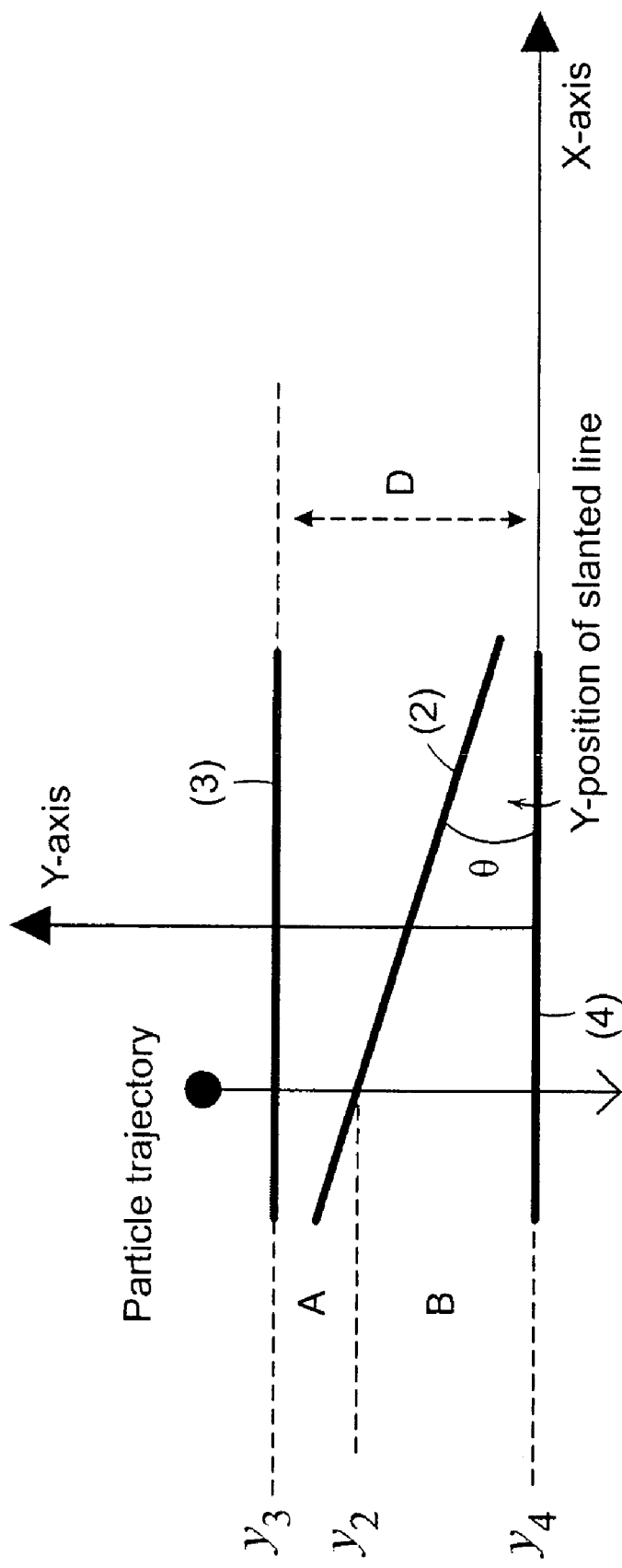

FIG. 5B illustrates the geometrical relationship of the SLB which may be employed in finding the position of the particle in the second (x) dimension. The position of the particle in the second (x) dimension may be obtained using the third (3), fourth (4), and either the first (1) or second (2) portions of the SLB. It should be appreciated that although FIG. 5B shows the third (3), fourth (4) and second (2) portions of the SLB being employed in finding the position of the particle in the first (z) dimension, the first (1) portion of the SLB may be employed instead of the second (2) portion.

The second (2) portion of the SLB comprises a sloped orientation with respect to the second (x) dimension, which may be represented by:

$$y = mx + b \quad [11]$$

where the slope m may be written in terms of angle θ, and substituting in for the values of b and y yields:

$$y_2 - y_4 = -\tan(\theta)x + \frac{D}{2} \quad [12]$$

Using the following geometrical relationship:

$$A = B + D \quad [13]$$

solving for x in equation [12] yields:

$$x = \frac{(A+B)}{\tan(\theta)} \left( \left( \frac{A}{A+B} \right) - \frac{1}{2} \right) \quad [14]$$

Substituting the y intercept values of A and B yields:

$$x = \frac{y_2 - y_4}{\tan(\theta)} \left( \frac{y_3 - y_2}{y_3 - y_4} - \frac{1}{2} \right) \quad [15]$$

Employing the relationships of equations [7] and [8] into equation [15] yields:

$$x = \frac{D}{\tan(\theta)} \left( \frac{t_2 - t_3}{t_4 - t_3} - \frac{1}{2} \right) \quad [16]$$

Therefore, with knowledge of the constant distance D between the third (3) and fourth (4) portions of the SLB, the angle θ defined by the orientation of the second (2) portion of the SLB with respect to the second (x) dimension, the timing values (FIG. 4D) of the particle passing through the second (2), third (3), and fourth (4) portions of the SLB, and the particle velocity, the position of the particle in the second (x) dimension may be obtained in real time.

It should be appreciated that although the above examples (FIGS. 5A and 5B) obtain the first (z) and second (x) dimensional positions with knowledge of the particle velocity, the position of the particle in the first (z), second (x), and third (y) dimension, as well as the particle velocity may be obtained simultaneously. For example, by utilizing the geometrical relationship of the various portions of the illumination pattern, and measured timing values, to generate four equations to solve the four unknowns. It should also be appreciated that the patterns shown in FIGS. 5A and 5B may be inverted, such that the position in the first (z) and second (x) dimensions may be utilized for determining the particle velocity.

Figure 5C:
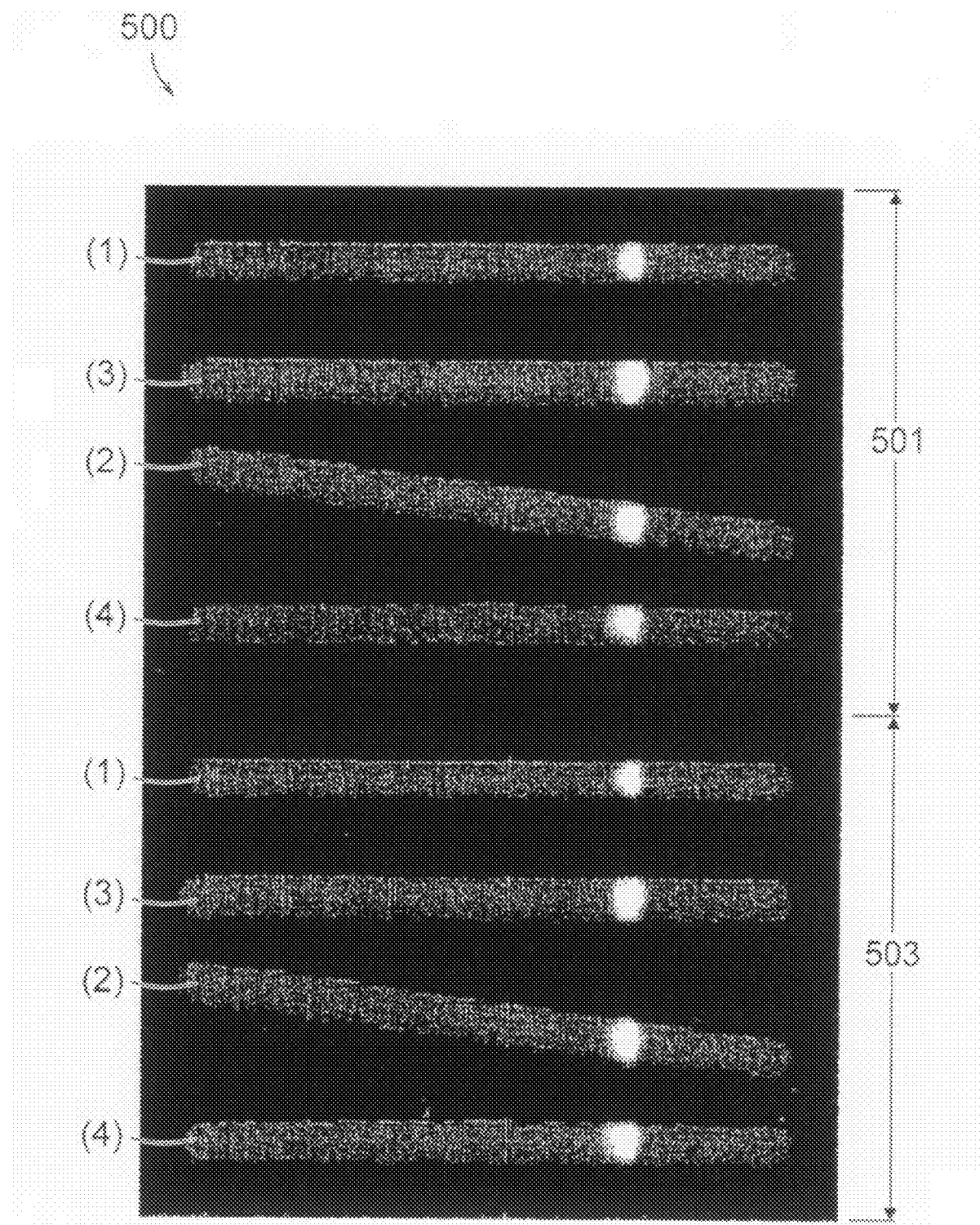
FIG. 5C is a schematic diagram of an example structured laser beam including multiple sections, according to an embodiment of the present invention.

FIG. 5C illustrates an illumination pattern 500 comprising a first section 501 and a second section 503. Each of the sections 501 and 503 may include identical illumination pattern sections (1)-(4). Using the configuration of the illumination pattern 500, a first temporal profile may be obtained via the first section 501 of the illumination pattern 500, as well as a second temporal profile via the second section 503 of the illumination pattern 500. Therefore, two sets of timing signals may be obtained. Employing the two sets of timing signals, an updated particle velocity may be obtained, using the methods for determining velocity as described above. Additionally, updated particle positions may be obtained using the second set of timing signals as well as the updated velocity. An acceleration, or time rate of change, may also be determined by comparing the determined velocities. Using multiple illumination pattern sections, the motion of the particle may be characterized. The characterization may also include changes in particle motion due to external forces exerted on the particle.

Figure 6:
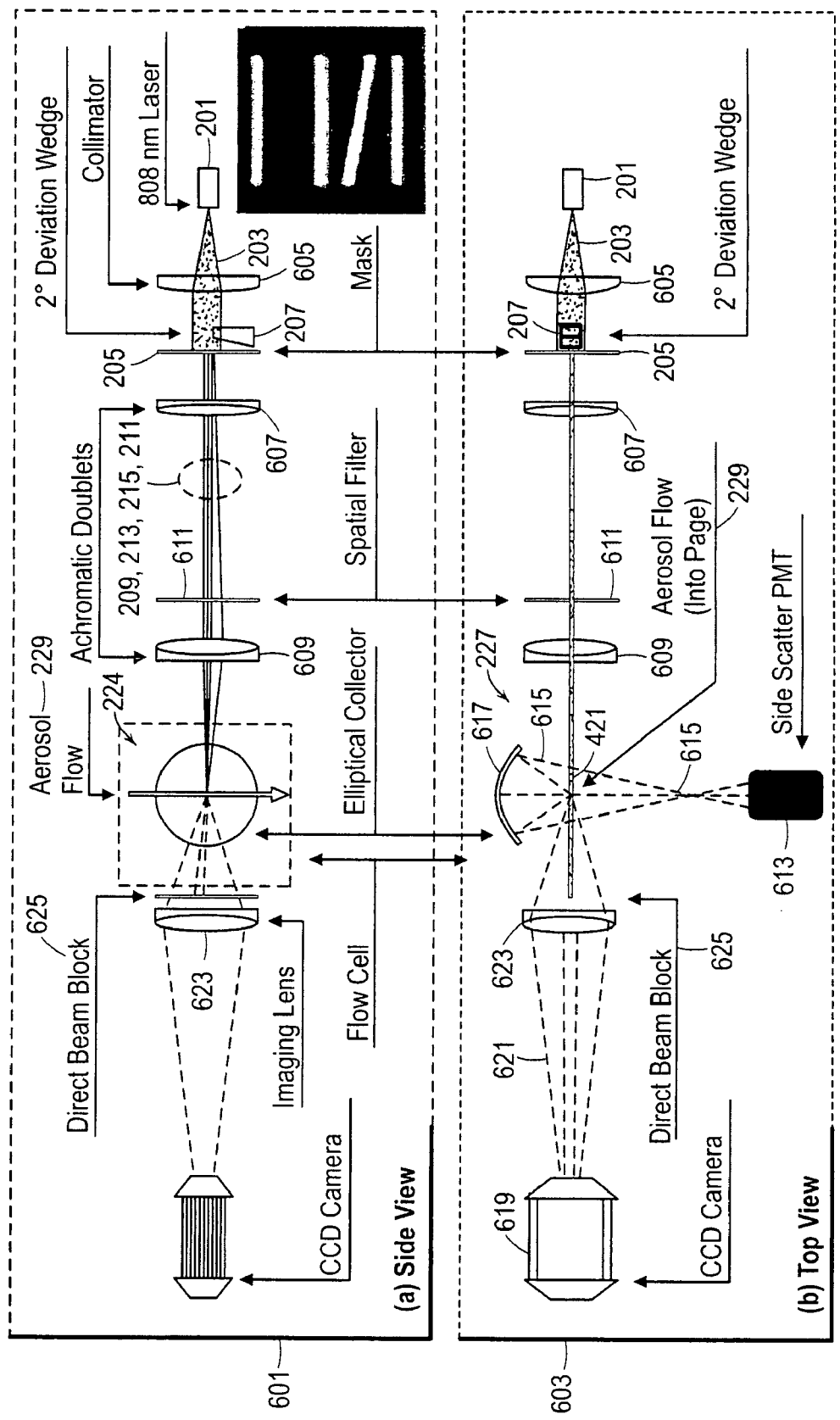
FIG. 6 is a detailed illustration of a structured laser beam detection system, according to an embodiment of the present invention.

FIG. 6 is a detailed schematic of side view 601 and top view 603 of an experimental set-up which may be employed in obtaining the timing values shown in FIG. 4D. The SLB depicted in FIG. 6 may be generated by using a mask 205 in conjunction with the optical delivery system. The optical delivery system may feature an 808 nm laser light source 201 providing an illuminating beam 203. In the experimental set up of FIG. 6, an air-slot mask 205 made of 0.050-mm thick NiCo was employed. The mask 205 includes of four air-slots whose dimensions are 0.15 mm high and 1.5 mm wide. The mask 205 may be illuminated with a 100 mW, single-mode fiber (not shown) which may be coupled to the 808 nm laser 201, and collimated using an air-spaced doublet 605. The air-spaced doublet 605 may produce a 7.14-mm ($1/e^2$) diameter beam illuminating the mask 205. The mask 205 may define the various portions of the SLB, or illumination pattern, for example portions 209, 211, 213, and 215. It should be appreciated that the mask shown in FIG. 6 is merely an example. Various mask designs may be employed to define a variety of illumination patterns. For example, the illumination pattern may include any number of portions, where the portions may further include any number of diverging or parallel portions.

Between the laser collimator 605 and the mask 205, an optical expanding element 207, for example a 2° deviation micro prism, may be employed to create the sloped first (1) and second (2) portions of the beam, 209 and 211 respectively, which may comprise a diverging orientation in the positive first (z) dimension. The light transmitted by the mask 205 may be re-imaged by an afocal system comprising of achromatic doublets 607 and 609, which may invert and de-magnify the final image by 3×. A spatial filter 611 which may employ two apertures, one for the two non-diverging portions of the illumination pattern (the third and fourth portions of the SLB) and another for the diverging portions of the illumination pattern (the first and second portions of the SLB) may be placed at the confocal plane. The spatial filter 611 may be used for eliminating undesirable fringing attributable to diffraction at the edges of the mask 205. The spatial filter 611 may also reduce stray light, and yields a clean, near Gaussian distribution normal to the long axis of the slits in the image plane.

The SLB optical delivery system may generate the illumination pattern in the center of an aerosol flow 229. An SLB detection system 613, similar to the light detector 237 of FIG. 2, may collect the elastic scattering 615 centered approximately 90° from the optical axis of the illumination system. The elastically scattered light 615 may be collected by at 70° half-angle, 5× paraxial magnification, elliptical collector 617. The elliptical collector 617 may comprise one focus at the sample volume region and re-image the scattered light 615 onto a photomultiplier tube (PMT) 613 located at an other ellipse focus, outside the sample volume 227. The PMT data may be sampled at 1MHz with a 14 bit computer controlled digitizer equipped with a current-to-voltage converter. The scattered light 615 includes a temporal profile which may be used to obtain timing values indicative of the particle position. Utilizing the timing values and the geometrical relationship between the various portions of the illumination pattern, the velocity and position of the particle in three dimensions may be obtained. It should be appreciated that FIG. 6 displays an alternative placement for the light detector 613, than the light detector 237 of FIG. 2. Therefore, the direction of light propagation, particle flow, and light detection, may be configured in a variety of ways.

To evaluate the SLB particle-localization capabilities, a second detection system 619 may be employed to detect the forward scattering 621 from aerosol particles. The forward light scattering 621 may be colleted by an f/4 camera lens 623 that may be located outside of the sample volume 227. The forward scattering light 621 may then be re-imaged onto a thermoelectrically controlled CCD camera 619. A vertical opaque strip, or beam block 625 may be used to block the direct beams when imaging the elastic scattering 621 from the aerosol particles. It should be appreciated that the second detection system 619 of the experimental setup is used merely as an independent verification of position-sensing performance. Therefore the second detection system 619 is not required in the overall SLB detection system (shown in FIGS. 2 and 6).

A computer may be used to synchronously collect PMT data (obtained from the SLB detector 613) with CCD data (obtained from the second detection system 619) for individual aerosol particles. The second forward-scattering imaging system 619 is utilized for obtaining an independent measurement for the verification of the lateral, x axis, or second dimension, position sensing capability of the SLB technique. The second detection and imaging system 619 is not part of the SLB technique.

Each particle that traverses the illumination pattern provided by the SLB has a forward scattering image collected with the CCD camera in addition to a photocurrent waveform collected from the PMT. The CCD pixel size corresponds to 3.8 μm per pixel at the reference plane inside the sample volume. The SLB PMT photocurrent may be traced on the CCD detected images for the particles flowing through the sample volume, in order to assess the position sensing capabilities of the SLB detections system.

Figure 7:
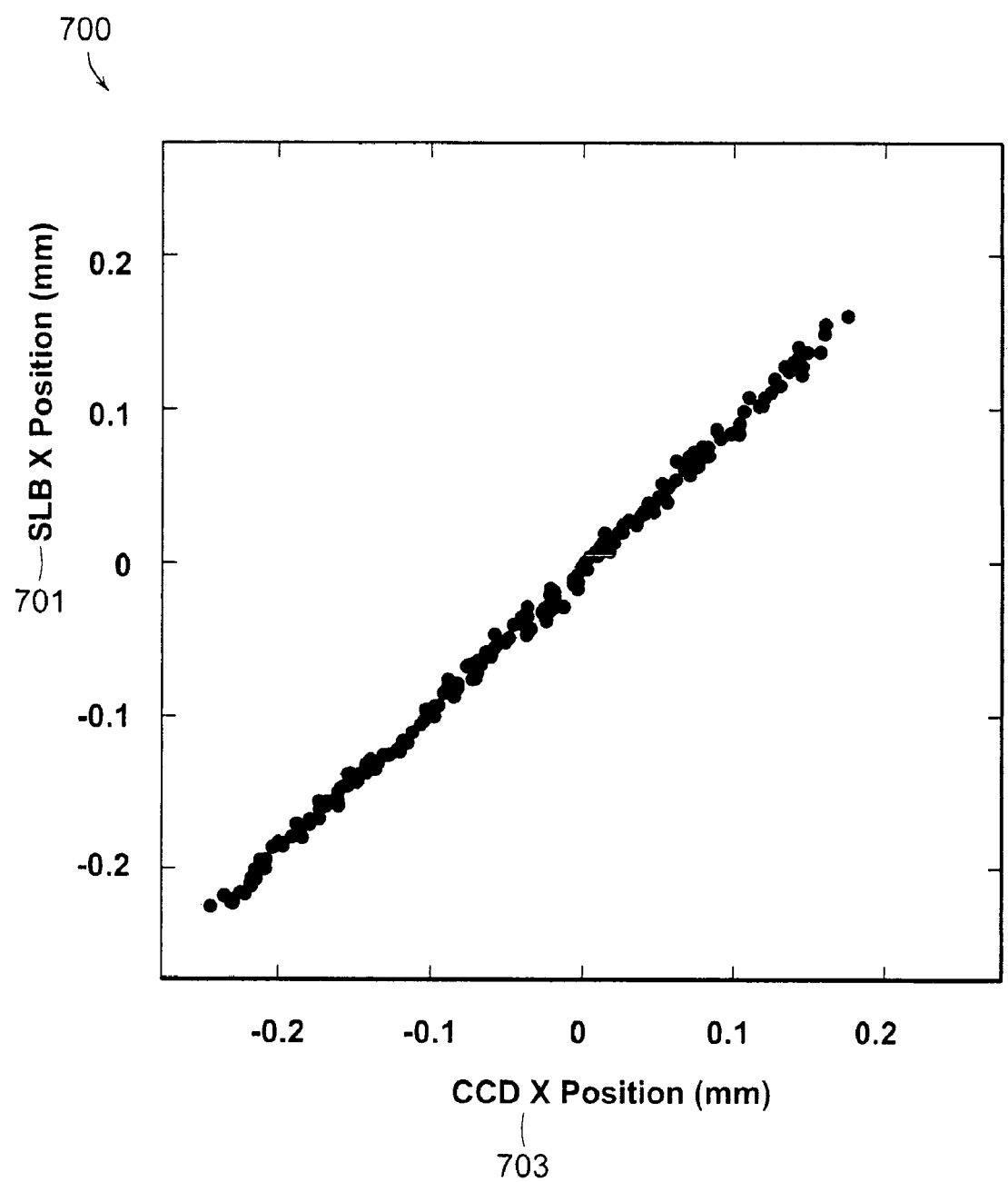
FIG. 7 is a graphical comparison of measured data providing an efficiency analysis, using the detection system of FIG. 6.

FIG. 7 depicts a graphical comparison 700 of the data measurements, for measuring the position of the particle in the first (x) dimension. The data measurements are obtained using the SLB measurement technique 701, and the second independent measurement system featuring the CCD camera 703. The graphical comparison 700 shows, that over the 500 μm x axis, or dimension, range of particle positions, the two methods of detection are in agreement. The root mean square difference between the SLB derived particle position and the forward scattering imaging system position data is 8 μm or 1.6% of the 500 μm range.

By recording position and amplitude data for a sufficient number of identical particles, it is possible to generate an instrument response map, which may greatly enhance resolution when sorting particles by some specific property (in the example embodiment, the specific property is the 90° side scattering cross section). This may be understood by considering FIGS. 8A and 8B.

FIG. 8A shows an example scatter plot of positions in the second (x) and first (z) dimensions for identical particles. In the present example, the determined positions were obtained by passing 1.96 μm polystyrene latex spheres (PSL) through the SLB illumination pattern. FIG. 8B shows the histograms for the signal amplitudes of this example data set. Since all of the test particles are exactly the same size, this histogram should ideally approximate a delta function; that is, all particles are expected to scatter with the same light intensity. The dotted histogram includes all the recorded data, and its width is attributable, in part, to the variation of both illumination and optical collection efficiency over the field of view.

Using the SLB data, small sub-regions [(i) and (ii) in FIG. 8A] of the flow may be selected in order to yield narrower histograms (as shown by the solid curves (i) and (ii) in FIG. 8B). Since identical PSL were utilized in obtaining the measured results, it may be reasonable to assume that the separation between the two solid histograms is due only to the variation in illumination and collection efficiency between the two regions. For example, the intensity of a beam is strongest in its center. Therefore, a particle passing through the center of the beam will result in a greater amount, or higher intensity, of elastic scattering, verses a particle passing through the beam in an off-centered location. This difference greatly reduces the effectiveness of the measurement technique and may result in incorrectly identifying the difference between multiple types of particles.

In an embodiment of the present invention, a solution for the off-center illumination of the particles may be obtained by utilizing the data obtained by the SLB detection system. The correction concept may be extended to the whole sampling region by subdividing the scatter plot area (FIG. 8A) into a suitable number of smaller regions. The average amplitude from each region may then be normalized to a suitable reference (in this case, the signal means) to generate the instrument response map.

Utilizing the instrument response map, the amplitude data of subsequent measurements may be scaled by a correction factor proportional to the value of the response map. The value of the response map may correspond to a similar region, or reading, of the subsequent measurement. Upon applying the correction factor, the overall amplitude histogram will approach the width of the localized histograms shown in FIG. 8B.

Figure 9:
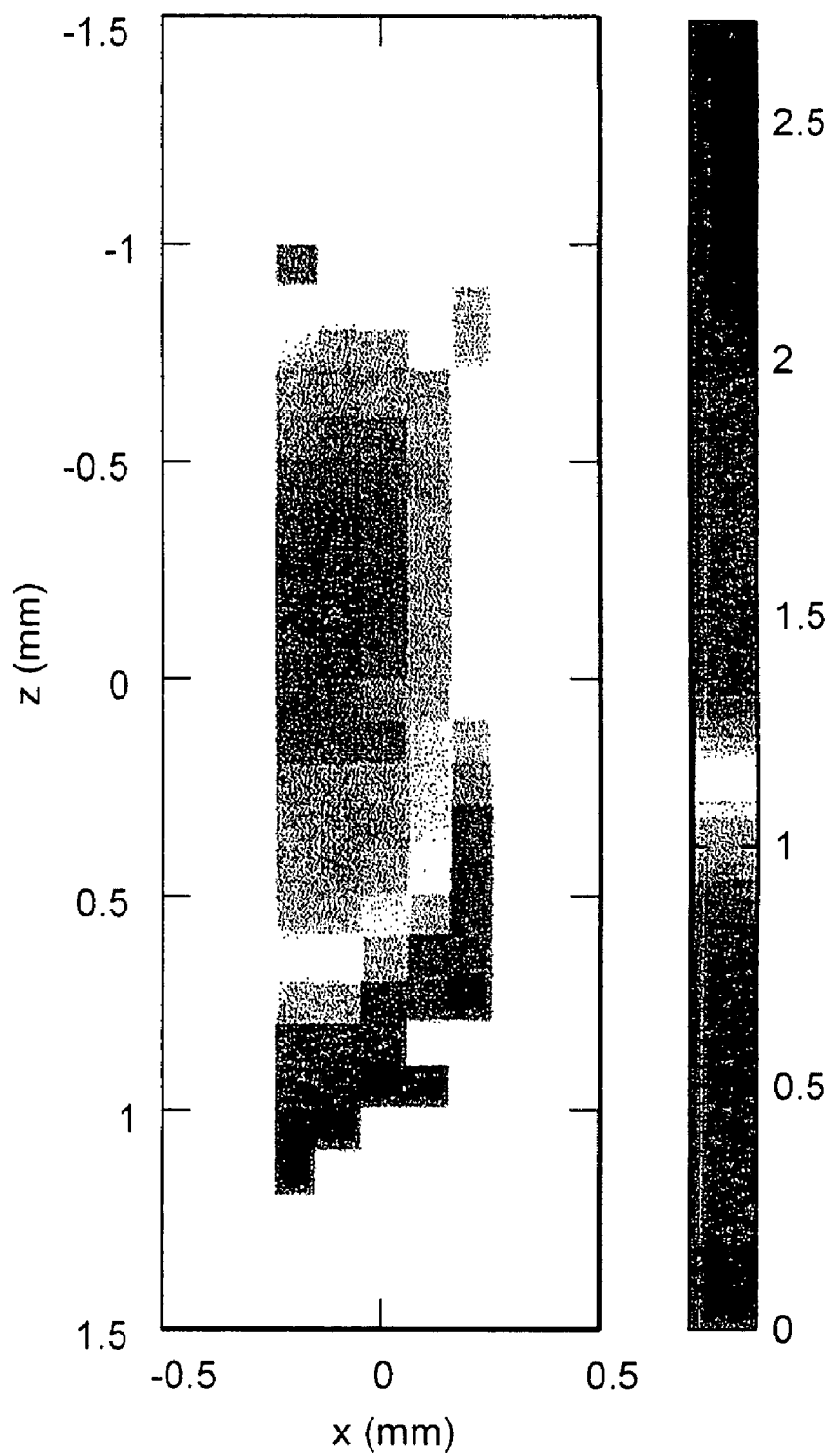
FIG. 9 is a graphical example of an instrument response map employed in determining correction factors, according to an embodiment of the present invention.

FIG. 9 is a response map generated in a manner described above, the calibration factors are displayed by color coding the regions in which the sample area has been subdivided.

Figure 10:
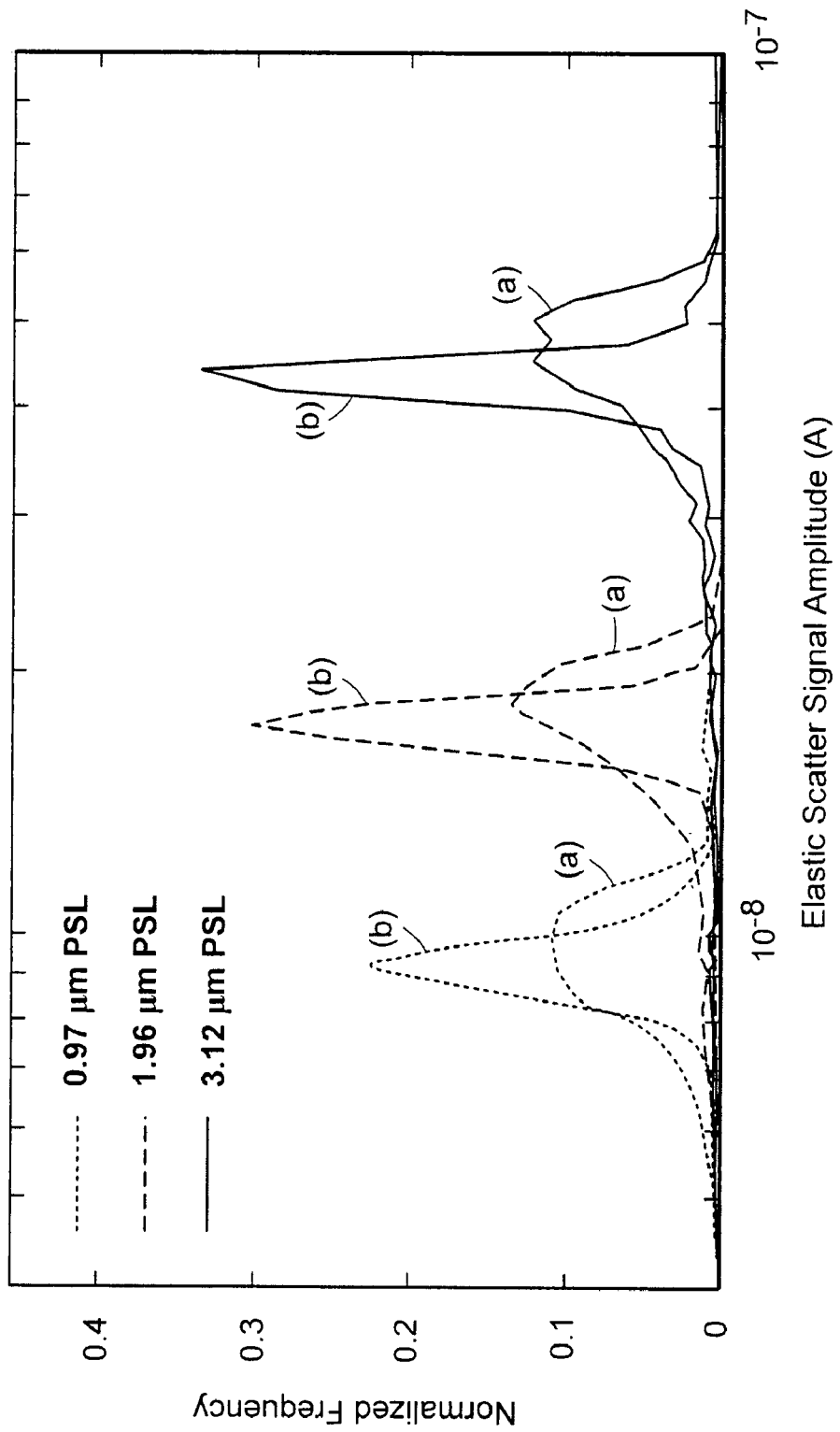
FIG. 10 is a graphical example of normalized measurement data obtained by applying the correction factors of FIG. 9, according to an embodiment of the present invention.

FIG. 10 is a plot of the normalized histograms of the elastic scattering signals from 0.966μm, 1.96μm, and 3.12μm diameter PSL spheres. The benefit of using the SLB data to correct for the spatial dependence of the instrument response function is evident from the data shown, as each of the respective PSL spheres comprise a near Gaussian scattering plot. The histograms labeled (a) are for the uncorrected, time-average photocurrent signals assuming a residence in time in the beam corresponding to the nominal flow velocity. Each of the histograms of the uncorrected data show significant tails on the low-amplitude side of the distributions corresponding to the signals collected from PSL spheres traversing the periphery of the elliptical collector's focal volume.

The histograms labeled (b) show the benefit of correcting for the spatial dependence of the instrument response function. The time-average photocurrent signal for these data sets was corrected for each individual particle's residence time in the beam as determined from the velocity measurement and for the spatial dependence of the instrument response function by using the correction map shown in FIG. 9. For all the particles sizes the histograms show size distribution widths that narrow by a factor between 2 and 3.

It should be appreciated that the normalization and correction methods described in FIGS. 9 and 10 may also be applied to a particle traveling downstream. For example, using the structured laser beam of FIG. 5C, a response map may be generated for particles passing through the first section 501 of the illumination pattern. Correction factors obtained from the response map may be applied to subsequent measurements from the same particles as the particles pass through the second section 503 of the illumination pattern. Therefore, the motion and position detection of a particle traveling downstream may be corrected in real time.

It should also be appreciated that the SLB detection system of FIG. 2 and FIG. 6 are merely shown as examples and that any other configuration may be used in the detection system. FIGS. 11-15 provide illustrative examples of a few of the many alternative configurations which may be employed.

Figure 11:
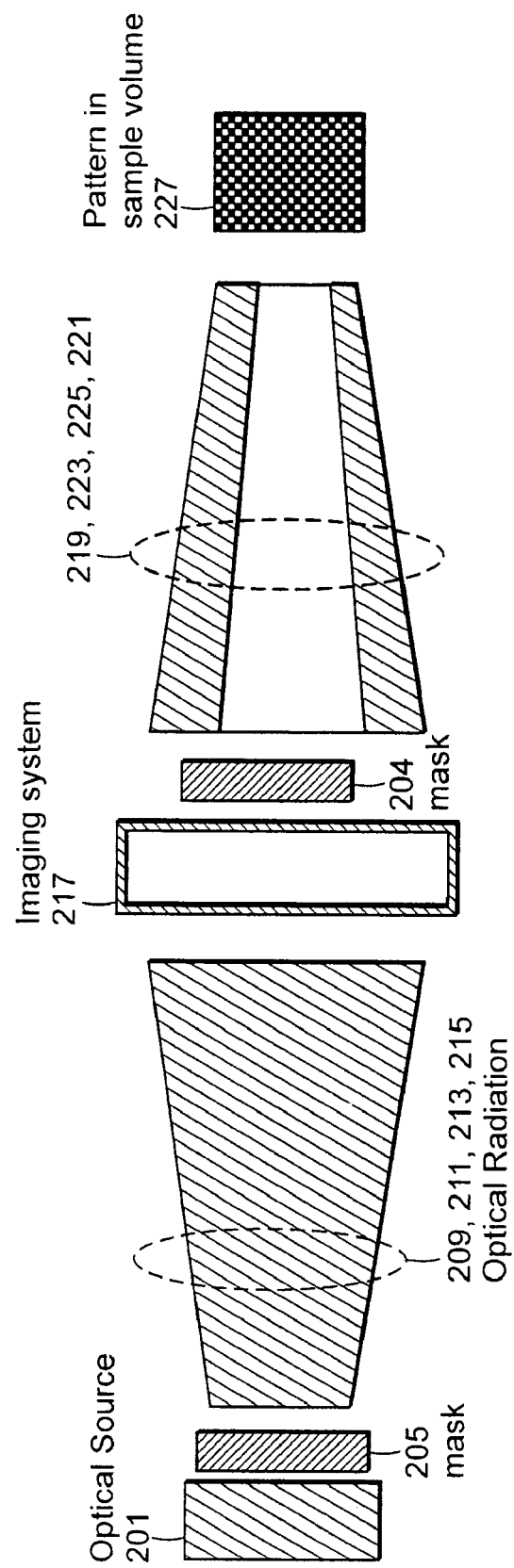
FIGS. 11-15 are schematic diagrams of example alternative configurations of the detections system of FIG. 2.

FIG. 11 is a schematic diagram that features a second masking element 204, that may placed after the imaging system 217 (as shown in FIG. 11) or before the imaging system 217 (not shown), that may be used to filter the SLB portions 219, 221, 223, and 225. The second masking element 204 may be a dark field, high pass, or apodizing filter that may be used to eliminate undesired intensity variations.

Figure 12:
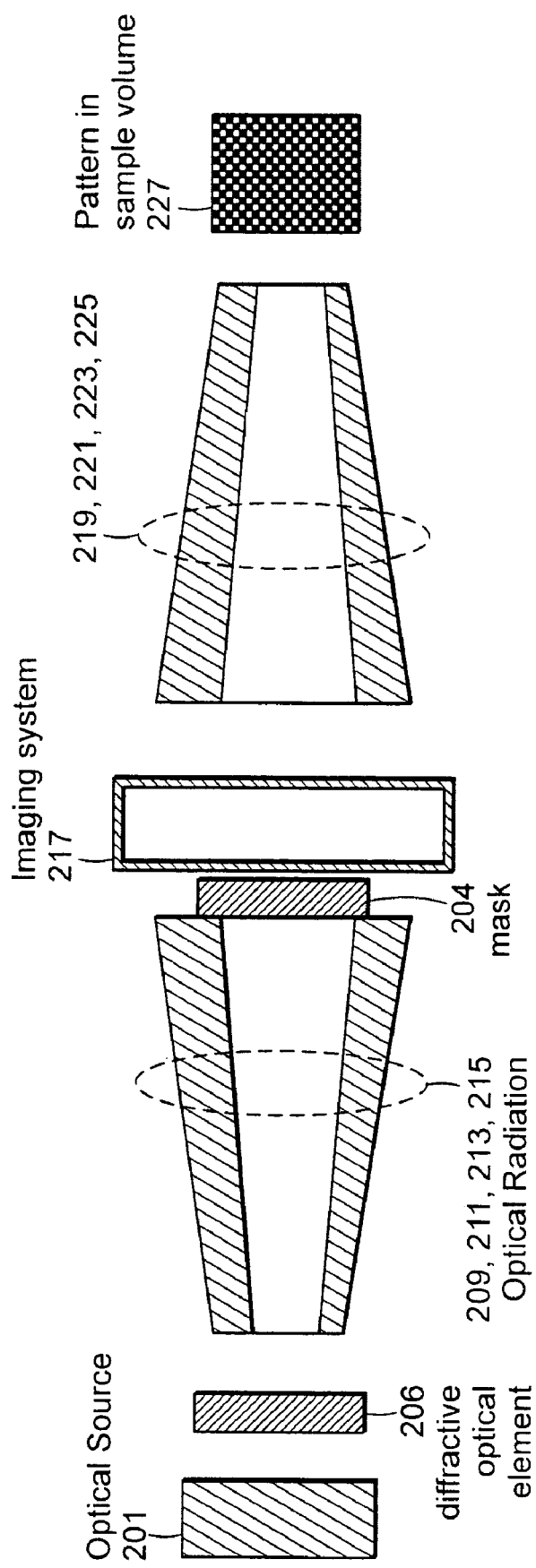

FIG. 12 is a schematic diagram that features a diffractive optical element 206 in place of the masking element 205. The diffractive optical element 206 may define the illumination pattern, or SLB. The diffractive optical element 206 may be in the form of a grating, beam splitter, a pattern generator, or any other form of diffractive optics known in the art. The system shown in FIG. 12 may or may not comprise the second masking element 204 situated either before or after the imaging system 217.

Figure 13:
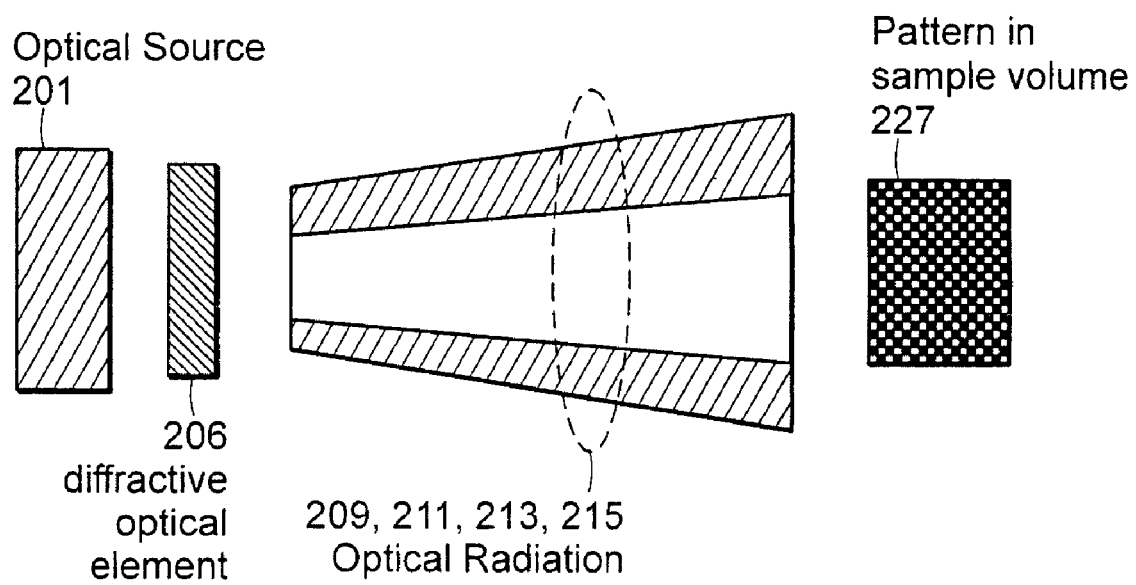

FIG. 13 is a schematic diagram that illustrates an alternative configuration of the detection system depicted in FIG. 12. In the detection system of FIG. 13, the imaging optics 217 have been omitted and the portions of the SLB 209, 211, 213, and 215 are applied directly to the sample volume 227. Although the imaging optics 217 may improve the efficiency of the detection system, the imaging optics 217 is not a require component of the system.

Figure 14:
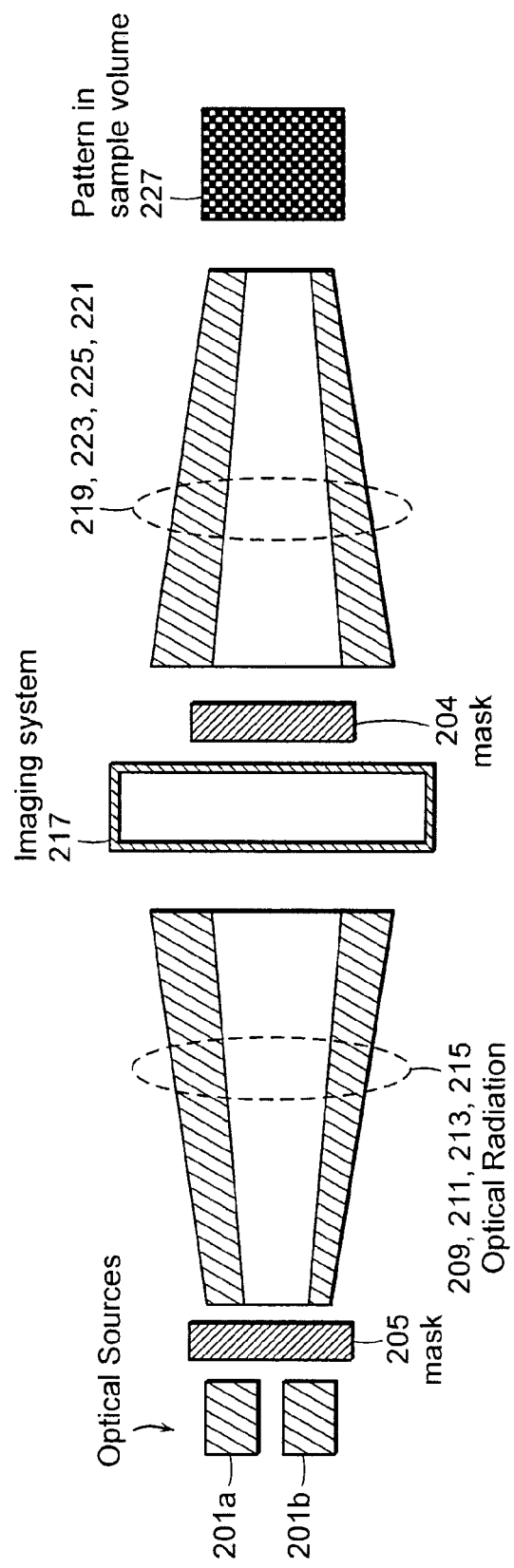

FIG. 14 is a schematic diagram that illustrates an alternative configuration featuring two light sources 201a and 201b. The light sources 201a and 201b may both be used to illuminate the masking element 205, in order to produce the SLB portions 209, 211, 213, and 215. The second masking element 204 may or may not be employed, and may either be situated before or after the imaging optics 217. The diffractive optical element 206 may be used in place of the masking element 205. The detection system of FIG. 14 may also be configured without the imaging system 217 such that the SLB portions 209, 211, 213, and 215 are applied directly to the sample volume 227.

Figure 15:
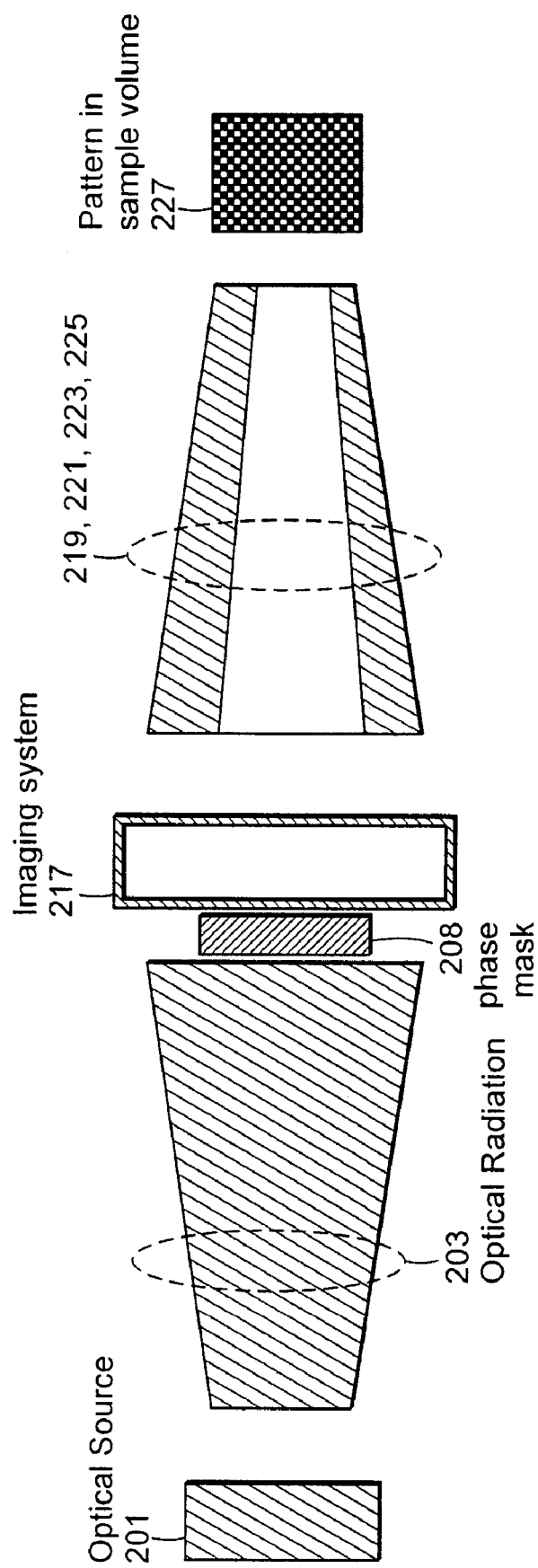

FIG. 15 is a schematic diagram that depicts an alternative detection system design where a phase mask 208 is used in place of the masking element 205, or diffractive optical element 206. The phase mask 208 may be used to define the various portions of the SLB, where instead of the SLB comprising regions of varying intensity, the SLB may comprise regions of varying polarization. A second imaging system (not shown) may be placed before the phase mask 208 in order to improve efficiency.

Various applications may utilize the SLB detection system and data normalization method discussed above. For example, particle classification techniques such as Laser-Induced Fluorescence (LIF), Laser-Induced Breakdown Spectroscopy (LIBS) and Spark-Induced Breakdown Spectroscopy (SIBS) may greatly benefit from detection and normalization techniques described above. The SLB detection system may reduce the amount of optical power necessary to illuminate the particle, since only portions of the SLB are utilized rather than the entire diameter of the beam. Furthermore, the SLB normalization method may reduce the occurrence of misclassification of particles by eliminating the problems associated with off-center beam illumination.

While this invention has been particularly shown and described with references to example embodiments thereof, it will be understood by those skilled in the art that various changes in form and details may be made therein without departing from the scope of the invention encompassed by the appended claims.

What is claimed is:

1. A method of determining a position of a particle in a flow, comprising:
   patterning an illuminating beam traveling in a first dimension to produce an illumination pattern in first, second, and third dimensions;
   passing a particle, traveling in the flow in the third dimension, through the illumination pattern;
   detecting a temporal profile of scattered light produced by the particle's passing through the illumination pattern; and
   determining from the temporal profile a position of the particle in the flow in at least two dimensions in a simultaneous manner.

2. The method of claim 1 wherein patterning the illuminating beam further comprises:
   forming a first portion of the illumination pattern at a first angle relative to an axis of propagation of the illuminating beam, and at a second angle relative to an axis along the second dimension;
   forming a second portion of the illumination pattern at a third angle relative to the axis of propagation of the illuminating beam, and at a fourth angle relative to the axis along the second dimension;
   forming a third portion of the illumination pattern at a sixth angle relative to an axis of propagation of the illuminating beam, and at a seventh angle relative to an axis along the second dimension; and
   forming a fourth portion of the illumination pattern at a eighth angle relative to an axis of propagation of the illuminating beam, and at a ninth angle relative to an axis along the second dimension.

3. The method of claim 2 further comprising:
   determining a velocity of the particle as a function of a geometrical relationship of at least two portions of a plurality of portions of the illumination pattern and a measurement of effects imparted in the temporal profile, caused by the particle's passing through the at least two portions of the plurality of portions of the illumination pattern.

4. The method of claim 3 further comprising:
   determining a time dependent position of the particle in the third dimension based on the velocity of the particle and a measurement of effects imparted in the temporal profile, caused by the particle's passing through at least one portion of the plurality of portions.

5. The method of claim 3 further comprising:
   determining the position of the particle in the second and/or first dimension, based on the velocity of the particle and a measurement of effects imparted in the temporal profile, caused by the particle's passing through at least one portion of the plurality of portions of the illumination pattern, and a geometrical relationship of the plurality of portions.

6. The method of claim 2 further comprising:
   simultaneously determining a velocity of the particle and a position of the particle in the first, and second dimensions, and a time dependent position of the particle in a third dimension, based on a measurement of effects imparted in the temporal profile, caused by the particle's passing through a plurality of portions of the illumination pattern, and a geometrical relationship of the plurality of portions.

7. The method of claim 1 wherein patterning the illuminating beam further comprises illuminating a masking element with at least one coherent or incoherent light source.

8. The method of claim 1 further comprising determining a position of the particle in a first and second dimension, a time dependent position in the third dimension, and a particle velocity.

9. The method of claim 8 further comprising:
   updating a previously determined velocity of the particle in the first and third dimension, and a particle acceleration in the second dimension;
   updating a previously determined position of the particle in the first and second dimensions, and the time dependent position in the third dimension, by measuring the same particle at a later time; and
   determining a time rate of change of the position of the particle in the first and second dimensions, and the time dependent position in the third dimension.

10. The method of claim 9 further comprising defining a motion of the particle by including changes in particle motion due to external forces exerted on the particle.

11. The method of claim 1 wherein detecting the temporal profile further comprises discriminating different particles in the particle flow.

12. The method of claim 1 wherein projecting the illuminating beam traveling in a first dimension to produce the illumination pattern in the first, second, and third dimensions, includes projecting it in a manner to define the illumination pattern with a pattern of varying intensity.

13. The method of claim 1 further comprising:
   passing multiple particles comprising a common property through multiple regions of the illumination pattern;
   creating a correction factor map of measured data in two dimensions based on temporal profiles detected responsive to the multiple particles passing through the illumination pattern;
   determining a plurality of calibration factors to correct a measurement of a particle that is off-center with respect to a center of the illuminating beam; and
   normalizing subsequent measurements relating to the common property with the plurality of calibration factors.

14. The method of claim 13 wherein normalizing subsequent measurements further comprises normalizing subsequent measurements employed in a spectroscopy analysis.

15. An apparatus for determining a position of a particle in a flow, comprising:
   a light source to generate an illuminating beam to travel in a first dimension, and to produce an illumination pattern in first, second, and third dimensions;
   a detector to detect a temporal profile of scattered light produced by the particle in the flow, traveling in the flow in the third dimension, passing through the illumination pattern; and
   a position determining unit to determine, from the temporal profile, a position of the particle in at least two dimensions in a simultaneous manner.

16. The apparatus of claim 15 wherein the light source is a coherent light source or an incoherent light source.

17. The apparatus of claim 15 further comprising a masking element configured to produce the illumination pattern once the masking element is illuminated by the light source.

18. The apparatus of claim 17 wherein the masking element is a mask or a diffractive optic.

19. The apparatus of claim 17 wherein the masking element is further configured to define the illumination pattern with a pattern of varying intensity.

20. The apparatus of claim 17 wherein the temporal profile is a first temporal profile, the masking element further comprising a first portion employed in obtaining the first temporal profile and at least one other portion employed in obtaining at least one second temporal profile to be detected at a later time.

21. The apparatus of claim 20 further comprising:
a velocity determining unit configured to determine a time rate of change in the at least two dimensions and characterize a velocity of the particle in the at least two dimensions; and
the position determining unit is further configured to refine a previously determined position of the particle in the at least two dimensions, from the first temporal profile, with the at least one other temporal profile, detected at a later time.

22. The apparatus of claim 20 wherein the processing unit is configured to simultaneously determine a position of the particle in the first dimension, second dimension, a time dependent position in the third dimension, and a particle velocity.

23. The apparatus of claim 22 further comprising:
a velocity determining unit configured to determine a rate of change of the position of the particle in the first and second dimension, and the time dependent position in the third dimension, and determine an updated particle velocity in the first and second dimension;
the position determining unit configured to refine a previously determined position of the particle in the first dimension, third dimension, and the time second dependent position in the dimension, with the at least one other temporal profile detected at a later time; and
an acceleration determining unit configured to determine a particle acceleration in the third dimension.

24. The apparatus of claim 23 wherein the position, velocity, and/or acceleration determining units are further configured to determine a motion of the particle with the inclusion of changes in particle motion due to external forces exerted on the particle.

25. The apparatus of claim 17, wherein the illumination pattern comprises a plurality of portions, further comprising an optical element, coupled to the masking element, configured to project at least one portion of the illumination pattern at a respective angle relative to an axis of propagation of the illuminating beam.

26. The apparatus of claim 23 wherein the position, velocity, and/or acceleration determining units are further configured to detect the presence of a biologic or chemical agent.

27. The apparatus of claim 23 wherein the position, velocity, and/or acceleration determining units are configured to determine a plurality of calibration factors for the normalization of subsequent measurements.

28. An apparatus for characterizing motion of a particle in a flow, comprising:
means for producing an illumination pattern in a first, second, and third dimension;
means for producing a temporal profile representing the position of the particle in the flow; and
means for determining the position of the particle in the flow, in the first and second dimension, and a time dependent position in the third dimension, in a simultaneous manner, based on the temporal profile.

29. The apparatus of claim 28 further comprising means for refining a previously determined position of the particle at a later time.

30. The apparatus of claim 28 further comprising means for normalizing subsequent measurements.

* * * * *